United States Patent
Huber et al.

(10) Patent No.: US 8,179,847 B2
(45) Date of Patent: May 15, 2012

(54) INTERACTIVE WHITE LIST PROMPTING TO SHARE CONTENT AND SERVICES ASSOCIATED WITH A FEMTOCELL

(75) Inventors: Kurt Donald Huber, Kennesaw, GA (US); Judson John Flynn, Decatur, GA (US); William Gordon Mansfield, Sugar Hill, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 527 days.

(21) Appl. No.: 12/275,925

(22) Filed: Nov. 21, 2008

(65) Prior Publication Data

US 2009/0285166 A1 Nov. 19, 2009

Related U.S. Application Data

(60) Provisional application No. 61/052,813, filed on May 13, 2008.

(51) Int. Cl.
*H04W 4/00* (2009.01)
(52) U.S. Cl. ......................... 370/329; 370/338; 370/341
(58) Field of Classification Search ........................ None
See application file for complete search history.

(56) References Cited

U.S. PATENT DOCUMENTS

| | | | |
|---|---|---|---|
| 5,864,764 A | 1/1999 | Thro et al. | |
| 6,052,594 A | 4/2000 | Chuang et al. | |
| 6,151,505 A | 11/2000 | Larkins | |
| 6,219,786 B1 | 4/2001 | Cunningham et al. | |
| 6,266,537 B1 | 7/2001 | Kashitani et al. | |
| 6,363,261 B1 | 3/2002 | Raghavan | |
| 6,483,852 B1 | 11/2002 | Jacquet et al. | |
| 6,484,096 B2 | 11/2002 | Wong | |
| 6,710,651 B2 | 3/2004 | Forrester | |
| 6,718,023 B1 | 4/2004 | Zolotov | |
| 7,080,139 B1 | 7/2006 | Briggs et al. | |
| 7,142,861 B2 | 11/2006 | Murai | |

(Continued)

FOREIGN PATENT DOCUMENTS

GB 2425921 A 11/2006

OTHER PUBLICATIONS

International Search Report and Written Opinion mailed Feb. 23, 2010, for PCT Application No. PCT/US2009/043846, 13 pages.

(Continued)

*Primary Examiner* — Chi Pham
*Assistant Examiner* — Soon-Dong Hyun
(74) *Attorney, Agent, or Firm* — Turocy & Watson LLP.

(57) ABSTRACT

System(s) and method(s) provide access management to femtocell service through access control list(s) (e.g., white list(s)). A white list(s) includes a set of subscriber station(s) identifier numbers, codes or tokens, and also can include additional fields for femtocell access management based on desired complexity. Various example aspects such as white list(s) management, maintenance and dissemination; pre-configuration; and inclusion of wireless device(s) or subscriber(s) are also provided. An access management component can facilitate interactive and automatic prompting of detected communication devices to facilitate granting access to content and/or services associated with the femtocell to a desired communication device(s) and adding a desired communication device(s) to the white list(s) associated with a femtocell, and to facilitate modifying or terminating access of the femtocell by a communication device(s) based in part on monitored activity of the communication device(s) with regard to femtocell access.

36 Claims, 17 Drawing Sheets

U.S. PATENT DOCUMENTS

| | | | |
|---|---|---|---|
| 7,146,153 | B2 | 12/2006 | Russell |
| 7,209,739 | B1 | 4/2007 | Narayanabhatla |
| 7,277,410 | B2 | 10/2007 | Horneman |
| 7,317,931 | B2 | 1/2008 | Guo |
| 7,496,383 | B2 | 2/2009 | Kurata |
| 7,613,444 | B2 * | 11/2009 | Lindqvist et al. ............ 455/403 |
| 7,623,857 | B1 | 11/2009 | O'Neil et al. |
| 7,633,910 | B2 | 12/2009 | Zhun et al. |
| 7,751,826 | B2 | 7/2010 | Gardner |
| 7,768,983 | B2 | 8/2010 | Nylander et al. |
| 7,885,644 | B2 | 2/2011 | Gallagher et al. |
| 7,929,537 | B2 * | 4/2011 | Vasudevan et al. .......... 370/392 |
| 7,929,970 | B1 | 4/2011 | Gunasekara |
| 7,941,144 | B2 * | 5/2011 | Nylander et al. ......... 455/435.1 |
| 7,995,994 | B2 | 8/2011 | Khetawat et al. |
| 2002/0098837 | A1 | 7/2002 | Ferrario et al. |
| 2002/0123365 | A1 | 9/2002 | Thorson |
| 2002/0142791 | A1 | 10/2002 | Chen et al. |
| 2003/0109271 | A1 | 6/2003 | Lewis et al. |
| 2003/0125044 | A1 | 7/2003 | Deloach |
| 2003/0142637 | A1 | 7/2003 | Khawer et al. |
| 2003/0153302 | A1 | 8/2003 | Lewis et al. |
| 2004/0111382 | A1 | 6/2004 | Haji-Ioannou |
| 2004/0258003 | A1 | 12/2004 | Kotot et al. |
| 2005/0003797 | A1 | 1/2005 | Baldwin |
| 2005/0009499 | A1 | 1/2005 | Koster |
| 2005/0026650 | A1 | 2/2005 | Russell |
| 2005/0075114 | A1 | 4/2005 | Dennison et al. |
| 2005/0144279 | A1 | 6/2005 | Wexelblat |
| 2005/0160276 | A1 | 7/2005 | Braun et al. |
| 2005/0172148 | A1 | 8/2005 | Ying |
| 2005/0177645 | A1 | 8/2005 | Dowling et al. |
| 2005/0250527 | A1 | 11/2005 | Jugl |
| 2005/0254451 | A1 | 11/2005 | Grosbach |
| 2006/0031387 | A1 | 2/2006 | Hamzeh et al. |
| 2006/0046647 | A1 | 3/2006 | Parikh et al. |
| 2006/0075098 | A1 | 4/2006 | Becker et al. |
| 2006/0223498 | A1 | 10/2006 | Gallagher et al. |
| 2007/0002844 | A1 | 1/2007 | Ali |
| 2007/0008894 | A1 | 1/2007 | Lynch et al. |
| 2007/0032225 | A1 | 2/2007 | Konicek et al. |
| 2007/0032269 | A1 | 2/2007 | Shostak |
| 2007/0074272 | A1 | 3/2007 | Watanabe |
| 2007/0097938 | A1 | 5/2007 | Nylander et al. |
| 2007/0097939 | A1 * | 5/2007 | Nylander et al. ............ 370/338 |
| 2007/0097983 | A1 | 5/2007 | Nylander et al. |
| 2007/0099561 | A1 | 5/2007 | Voss |
| 2007/0124802 | A1 | 5/2007 | Anton et al. |
| 2007/0155421 | A1 | 7/2007 | Alberth et al. |
| 2007/0167175 | A1 | 7/2007 | Wong |
| 2007/0183427 | A1 * | 8/2007 | Nylander et al. ......... 370/395.2 |
| 2007/0184815 | A1 | 8/2007 | Aebi |
| 2007/0199076 | A1 | 8/2007 | Rensin et al. |
| 2007/0258418 | A1 | 11/2007 | Wurtenberger et al. |
| 2007/0270152 | A1 * | 11/2007 | Nylander et al. ............ 455/445 |
| 2007/0287501 | A1 | 12/2007 | Hoshina |
| 2008/0076392 | A1 | 3/2008 | Khetawat et al. |
| 2008/0076393 | A1 | 3/2008 | Khetawat et al. |
| 2008/0076419 | A1 | 3/2008 | Khetawat et al. |
| 2008/0076420 | A1 | 3/2008 | Khetawat et al. |
| 2008/0076425 | A1 | 3/2008 | Khetawat et al. |
| 2008/0081636 | A1 | 4/2008 | Nylander et al. |
| 2008/0132239 | A1 | 6/2008 | Khetawat et al. |
| 2008/0133742 | A1 | 6/2008 | Southiere et al. |
| 2008/0151807 | A1 | 6/2008 | Meier et al. |
| 2008/0168099 | A1 | 7/2008 | Skaf |
| 2008/0181184 | A1 | 7/2008 | Kezys |
| 2008/0207170 | A1 | 8/2008 | Khetawat et al. |
| 2008/0242280 | A1 | 10/2008 | Shapiro et al. |
| 2008/0244148 | A1 | 10/2008 | Nix et al. |
| 2008/0281687 | A1 | 11/2008 | Hurwitz et al. |
| 2008/0299984 | A1 | 12/2008 | Shimomura |
| 2008/0299992 | A1 | 12/2008 | Eitan et al. |
| 2008/0305801 | A1 | 12/2008 | Burgess et al. |
| 2009/0037973 | A1 | 2/2009 | Gustave et al. |
| 2009/0047945 | A1 | 2/2009 | Zhang |
| 2009/0061873 | A1 | 3/2009 | Bao et al. |
| 2009/0082010 | A1 | 3/2009 | Lee |
| 2009/0082020 | A1 | 3/2009 | Ch'ng et al. |
| 2009/0092096 | A1 | 4/2009 | Czaja |
| 2009/0092097 | A1 | 4/2009 | Nylander et al. |
| 2009/0093232 | A1 | 4/2009 | Gupta et al. |
| 2009/0094351 | A1 | 4/2009 | Gupta et al. |
| 2009/0094680 | A1 | 4/2009 | Gupta et al. |
| 2009/0097436 | A1 | 4/2009 | Vasudevan et al. |
| 2009/0111499 | A1 | 4/2009 | Bosch |
| 2009/0122773 | A1 | 5/2009 | Gogic |
| 2009/0124262 | A1 | 5/2009 | Vela et al. |
| 2009/0131050 | A1 | 5/2009 | Osborn |
| 2009/0135749 | A1 | 5/2009 | Yang |
| 2009/0135794 | A1 | 5/2009 | Su et al. |
| 2009/0156213 | A1 | 6/2009 | Spinelli et al. |
| 2009/0163216 | A1 * | 6/2009 | Hoang et al. .................. 455/450 |
| 2009/0163224 | A1 | 6/2009 | Dean |
| 2009/0164547 | A1 | 6/2009 | Ch'ng et al. |
| 2009/0170528 | A1 | 7/2009 | Bull et al. |
| 2009/0191844 | A1 | 7/2009 | Morgan et al. |
| 2009/0191845 | A1 * | 7/2009 | Morgan et al. ................ 455/411 |
| 2009/0210324 | A1 | 8/2009 | Bhogal |
| 2009/0215452 | A1 | 8/2009 | Balasubramanian et al. |
| 2009/0221303 | A1 | 9/2009 | Soliman |
| 2009/0233574 | A1 | 9/2009 | Shinozaki |
| 2009/0245176 | A1 | 10/2009 | Balasubramanian et al. |
| 2009/0253421 | A1 | 10/2009 | Camp et al. |
| 2009/0253432 | A1 | 10/2009 | Willey et al. |
| 2009/0279701 | A1 | 11/2009 | Moisand et al. |
| 2009/0291667 | A1 | 11/2009 | Vakil et al. |
| 2010/0022266 | A1 | 1/2010 | Villier |
| 2010/0040026 | A1 | 2/2010 | Melkesetian |
| 2010/0260068 | A1 | 10/2010 | Bhatt et al. |
| 2011/0200022 | A1 | 8/2011 | Annamalai |

OTHER PUBLICATIONS

OA dated Dec. 31, 2009 for U.S. Appl. No. 11/457,129, 16 pages.
OA dated Apr. 17, 2009 for U.S. Appl. No. 11/276,269, 15 pages.
OA dated Nov. 4, 2008 for U.S. Appl. No. 11/276,269, 15 pages.
OA dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
International Search Report and Written Opinion dated Oct. 27, 2009 for PCT Application U.S. Appl. No. PCT/US2009/043861, 14 Pages.
OA dated Mar. 29, 2011 for U.S. Appl. No. 12/276,002, 37 pages.
OA dated Apr. 13, 2011 for U.S. Appl. No. 12/276,058, 40 pages.
OA dated Apr. 19, 2011 for U.S. Appl. No. 12/276,238, 22 pages.
OA dated May 5, 2011 for U.S. Appl. No. 12/275,015, 32 pages.
OA dated Jun. 14, 2011 for U.S. Appl. No. 12/275,878, 35 pages.
OA dated Jun. 22, 2011 for U.S. Appl. No. 12/484,072, 38 pages.
OA dated Jul. 7, 2011 for U.S. Appl. No. 12/276,257, 24 pages.
OA dated Jun. 8, 2011 for U.S. Appl. No. 12/484,026, 30 pages.
OA dated Aug. 18, 2011 for U.S. Appl. No. 12/275,416, 39 pages.
OA dated Sep. 14, 2011 for U.S. Appl. No. 12/276,002, 35 pages.
OA dated Oct. 5, 2011 for U.S. Appl. No. 12/276,058, 37 pages.
OA dated Oct. 6, 2011 for U.S. Appl. No. 12/465,483, 50 pages.
OA dated Oct. 4, 2011 for U.S. Appl. No. 12/484,135, 44 pages.
OA dated Jul. 21, 2011 for U.S. Appl. No. 12/175,293, 30 pages.
OA dated Jan. 5, 2011 for U.S. Appl. No. 12/465,585, 43 pages.
OA dated Nov. 30, 2011 for U.S. Appl. No. 12/275,878, 38 pages.
OA dated Dec. 1, 2011 for U.S. Appl. No. 12/275,996, 44 pages.
OA dated Oct. 25, 2011 for U.S. Appl. No. 12/465,580, 39 pages.
OA dated Nov. 8, 2011 for U.S. Appl. No. 12/465,468, 50 pages.
OA dated Dec. 28, 2011 for U.S. Appl. No. 12/175,293, 38 pages.
OA dated Nov. 21, 2011 for U.S. Appl. No. 12/484,026, 37 pages.
OA dated Dec. 14, 2011 for U.S. Appl. No. 12/484,072, 44 pages.
OA dated Nov. 1, 2011 for U.S. Appl. No. 12/816,087, 33 pages.

* cited by examiner

INTERACTIVE WHITE LIST PROMPTING TO SHARE CONTENT AND SERVICES ASSOCIATED WITH A FEMTOCELL

CROSS-REFERENCE TO RELATED APPLICATION

This application claims the benefit of U.S. Provisional Patent application Ser. No. 61/052,813 entitled "MANAGEMENT OF ACCESS TO FEMTO CELL COVERAGE" and filed on May 13, 2008. The entirety of the above-referenced application is incorporated by reference herein.

TECHNICAL FIELD

The subject innovation generally relates to wireless communications, and, more particularly, to interactive client management of a white list associated with a femtocell.

BACKGROUND

Femtocells—building-based wireless access points interfaced with a wired broadband network—are generally deployed to improve indoor wireless coverage provided by a wireless network operator. Femtocells typically operate in licensed portions of the electromagnetic spectrum, and generally offer plug-and-play installation; e.g., automatic configuration of femto access point. Improved indoor coverage includes stronger signal and improved reception (e.g., voice or sound), ease of session or call initiation and session or call retention as well. Coverage of a femtocell, or femto AP, is intended to be confined within the bounds of an indoor compound, in order to mitigate interference among mobile stations covered by a macro cell and terminals covered by the femto AP. Additionally, confined coverage can reduce crosstalk among terminals serviced by disparate, neighboring femtocells as well.

Coverage improvements via femtocells also can mitigate customer attrition as long as a favorable subscriber perception regarding voice coverage and other data services with substantive delay sensitivity is attained. A positive customer experience can depend on adequate access management to femtocell service.

It can be desirable to encourage communication devices to utilize a femtocell owned/operated by a subscriber, and content and services available via the femtocell, as it can facilitate communication of information between communication devices and respective users of those communication devices and/or can generate income for the subscriber that owns/operates the femtocell. It also can be desirable to manage access of wireless communication devices to a femtocell and associated content and services to facilitate efficient use of bandwidth, and content and services, associated with the femtocell and ensure that desired users can access the femtocell.

SUMMARY

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The subject innovation provides system(s) and method(s) to manage access to femtocell service through access control list(s), or "white list(s)." In an aspect, the white list(s) can be configured via a networked interface that can facilitate access management to a femtocell (e.g., femto access point). A white list(s) can include a set of subscriber station(s) identifier numbers, codes or tokens, and can also include additional fields, that can contain information respectively associated with communication devices to facilitate femtocell access management based at least in part on desired complexity.

In an aspect, the femtocell can facilitate automatically querying a subscriber station(s) (e.g., cellular phone, computer, . . . ), which is detected in a femtocell coverage area of the femtocell, to prompt the communication device(s) to access or request access to the femtocell and content and/or services associated therewith to facilitate automatically populating the white list(s) with desired communication devices. In one aspect, the femtocell can include an access management component that can employ interactive and automatic prompting of detected communication devices to facilitate managing access to femtocell coverage and content and/or services associated therewith. The access management component can automatically generate and transmit a query to a detected communication device to prompt the communication device to access or request to access the femtocell and associated content and/or services and to be entered on the white list(s) of the femtocell. In response to the query, the communication device can opt in to access the femtocell and associated services, or subset thereof, and to be entered on the white list(s) on a permanent basis or temporary basis, or can opt out of accessing the femtocell and associated services, where information related to the communication device, which has opted out or has been denied access to the femtocell, can be stored in a black list(s) of the femtocell.

In one aspect, the access management component can determine whether to grant access to the femtocell and an associated subset of content and/or services to a communication device based at least in part on slot availability of the white list(s) (and the femtocell) and other predefined access criteria, information contained in the white list(s), and/or a request (e.g., request to opt in to access the femtocell on a temporary basis, request to opt in to access the femtocell on a permanent basis) received from the communication device. In another aspect, when a communication device is being granted access to the femtocell, the access management component can automatically prompt (e.g., via a query) the communication device to indicate the type of access, type of content, and/or type of service(s) desired by the communication device. Also, when the communication device is granted access to the femtocell, the access management component can update the white list(s) to store information (e.g., identification information, device information, bandwidth allocation, subset of content and/or services for which access is granted, and/or other information) related to the communication device in the white list(s). When granted access to the femtocell and subset of content and/or services, the communication device can communicate with other communication devices and/or can access and utilize the subset of content and/or services provided via the femtocell (e.g., via content providers and/or service providers connected to the femtocell).

In another aspect, the access management component can monitor activity of communication devices that are accessing the femtocell to facilitate determining whether a communication device(s) is accessing the subset of content and/or services for which access has been granted. If the access management component observes that a communication device(s) has not been accessing the subset of content and/or services, or a portion thereof, for a predefined period of time, the access management component can facilitate generating and transmitting a query to the communication device(s) to prompt the communication device (and associated user) to indicate whether the communication device(s) desires to continue access to the subset of content and/or services, modify access to the subset of content and/or services, or terminate access to the subset of content and/or services. Based at least in part on the response from the communication device(s), the access management component can continue access, modify access, or terminate access of the subset of content and/or services by the communication device(s) to facilitate efficiently managing access to the femtocell.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention may be employed. Other aspects, advantages and novel features of the invention will become apparent from the following detailed description of the invention when considered in conjunction with the drawings.

DETAILED DESCRIPTION

Figure 1:
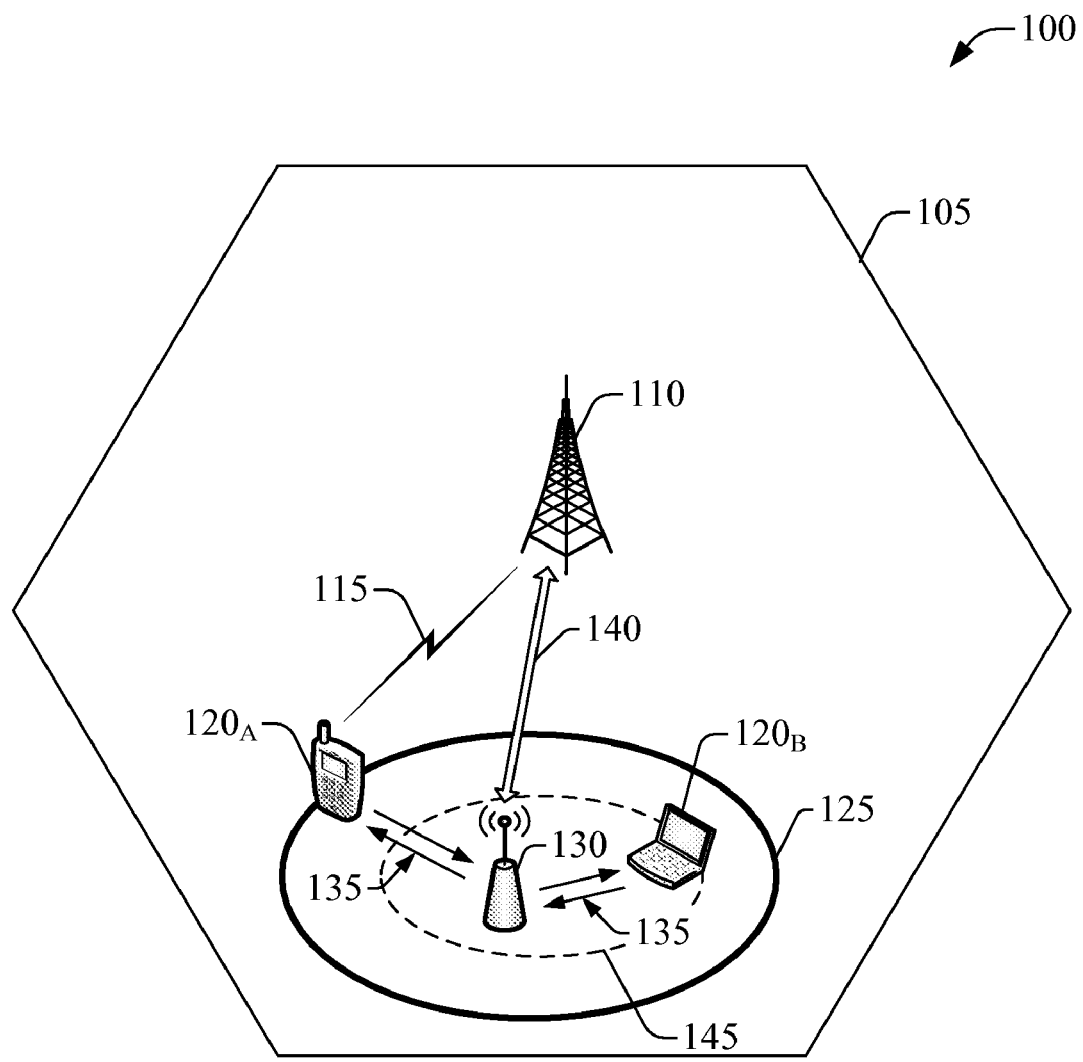
FIG. 1 a schematic deployment of a macro cell and a femtocell for wireless coverage in accordance with aspects described herein.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component," "system," "platform," and the like can refer to a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," "subscriber station," "communication device," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B," "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

Furthermore, the terms "user," "subscriber," "customer," "consumer," "prosumer," "agent," and the like are employed interchangeably throughout the subject specification, unless context warrants particular distinction(s) among the terms. As utilized herein, the term "prosumer" indicate the following contractions: professional-consumer and producer-consumer.

The following abbreviations are relevant to the subject specification.

3G Third Generation
3GPP Third Generation Partnership Project
AGPS Assisted GPS
AP Access Point
ADSL Asymmetric Digital Subscriber Line
AWS Advanced Wireless Services
BRAS Broadband Remote Access Server
BTA Basic Trading Area
CN Core Network
CS Circuit-Switched
CSCF Call Session Control Function
CPE Customer Premise Equipment
CPN Customer Premise Network
DHCP Dynamic Host Configuration Protocol
DSL Digital Subscriber Line
DSLAM Digital Subscriber Line Access Multiplexer
E911 Enhanced 911
FCC Federal Communications Commission
FL Forward Link
GGSN Gateway GPRS Service Node
GPRS General Packet Radio Service
GPS Global Positioning System
GW Gateway
HAP Home Access Point
HSS Home Subscriber Server
ISDN Integrated Services Digital Network
UE User Equipment
UTRAN Universal Terrestrial Radio Access Network
IMS IP Multimedia Subsystem
IP Internet Protocol
ISP Internet Service Provider
MSA Metropolitan Statistical Areas
MSISDN Mobile Subscriber ISDN Number
MTA Major Trading Areas
NAT Network Address Translation
NTP Network Time Protocol
O&M Operation and Maintenance
PC Personal Computer
PCS Personal Communications Service
PS Packet-Switched
PSTN Public Switched Telephone Network
RAN Radio Access Network
RBS Radio Base Station
RL Reverse Link
RNC Radio Network Controller
RSA Rural Service Area
SGSN Serving GPRS Support Node
SIP Session Initiation Protocol
USSD Unstructured Supplementary Service Data
VPN Virtual Private Network
WAP Wireless Application Protocol
XDSL Asynchronous-DSL or Synchronous-DSL Referring to the drawings, FIG. 1 illustrates a schematic wireless environment 100 (e.g., a network) in which a femtocell can exploit various aspects of the subject innovation in accordance with the disclosed subject matter. In wireless environment 100, area 105 can represent a coverage macro cell which can be served by base station 110. Macro coverage is generally intended for outdoors locations for servicing mobile wireless devices, like UE $120_A$, and such coverage is achieved via a wireless link 115. In an aspect, UE 120 can be a 3GPP Universal Mobile Telecommunication System (UMTS) mobile phone.

Within macro coverage cell 105, a femtocell 145, served by a femto access point 130, can be deployed. A femtocell typically can cover an area 125 that is determined, at least in part, by transmission power allocated to femto AP 130, path loss, shadowing, and so forth. Coverage area typically can be spanned by a coverage radius that ranges from 20 to 50 meters. Confined coverage area 145 is generally associated with an indoors area, or a building, which can span about 5000 sq. ft. Generally, femto AP 130 typically can service a number (e.g., a few or more) wireless devices (e.g., subscriber station $120_B$) within confined coverage area 145. In an aspect, femto AP 130 can integrate seamlessly with substantially any PS-based and CS-based network; for instance, femto AP 130 can integrate into an existing 3GPP Core via conventional interfaces like Iu-CS, Iu-PS, Gi, Gn. In another aspect, femto AP 130 can exploit high-speed downlink packet access in order to accomplish substantive bitrates. In yet another aspect, femto AP 130 has a LAC (location area code) and RAC (routing area code) that can be different than the underlying macro network. These LAC and RAC are used to identify subscriber station location for a variety of reasons, most notably to direct incoming voice and data traffic to appropriate paging transmitters.

As a subscriber station, e.g., UE $120_A$, leaves macro coverage (e.g., cell 105) and enters femto coverage (e.g., area 125), as illustrated in environment 100, UE $120_A$ can attempt to attach to the femto AP 130 through transmission and reception of attachment signaling, effected via a FL/RL 135; in an aspect, the attachment signaling can include a Location Area Update (LAU) and/or Routing Area Update (RAU). Attachment attempts are a part of procedures to ensure mobility, so voice calls and sessions can continue even after a macro-to-femto transition or vice versa. It is to be noted that UE 120 can be employed seamlessly after either of the foregoing transitions. Femto networks are also designed to serve stationary or slow-moving traffic with reduced signaling loads compared to macro networks. A femto service provider (e.g., an entity that commercializes, deploys, and/or utilizes femto access point 130) therefore can be inclined to minimize unnecessary LAU/RAU signaling activity at substantially any opportunity to do so, and through substantially any available means. It is to be noted that substantially any mitigation of unnecessary attachment signaling/control can be advantageous for femtocell operation. Conversely, if not successful, UE 120 generally can be commanded (through a variety of communication means) to select another LAC/RAC or enter "emergency calls only" mode. It is to be appreciated that this attempt and handling process can occupy significant UE battery, and femto AP capacity and signaling resources as well.

When an attachment attempt is successful, UE 120 can be allowed on femtocell 125 and incoming voice and data traffic can be paged and routed to the subscriber station through the femto AP 130. It is to be noted also that data traffic is typically routed through a backhaul broadband wired network backbone 140 (e.g., optical fiber backbone, twisted-pair line, T1/E1 phone line, DSL, or coaxial cable). To this end, femto AP 130 can be connected to the broadband backhaul network backbone 140 via a broadband modem (not shown).

It is to be noted that as a femto AP 130 generally can rely on a backhaul network backbone 140 for routing and paging, and for packet communication, substantially any quality of service can handle heterogeneous packetized traffic. Namely, packet flows established for wireless communication devices (e.g., terminals $120_A$ and $120_B$) served by femto AP 130, and for devices served through the backhaul network pipe 140. It is to be noted that to ensure a positive subscriber experience, or perception, it is desirable for femto AP 130 to maintain a high level of throughput for traffic (e.g., voice and data) utilized on a mobile device for one or more subscribers while in the presence of external, additional packetized, or broadband, traffic associated with applications (e.g., web browsing, data transfer (e.g., content upload), and the like) executed in devices within the femto coverage area (e.g., area 125 or area 145).

Figure 2:
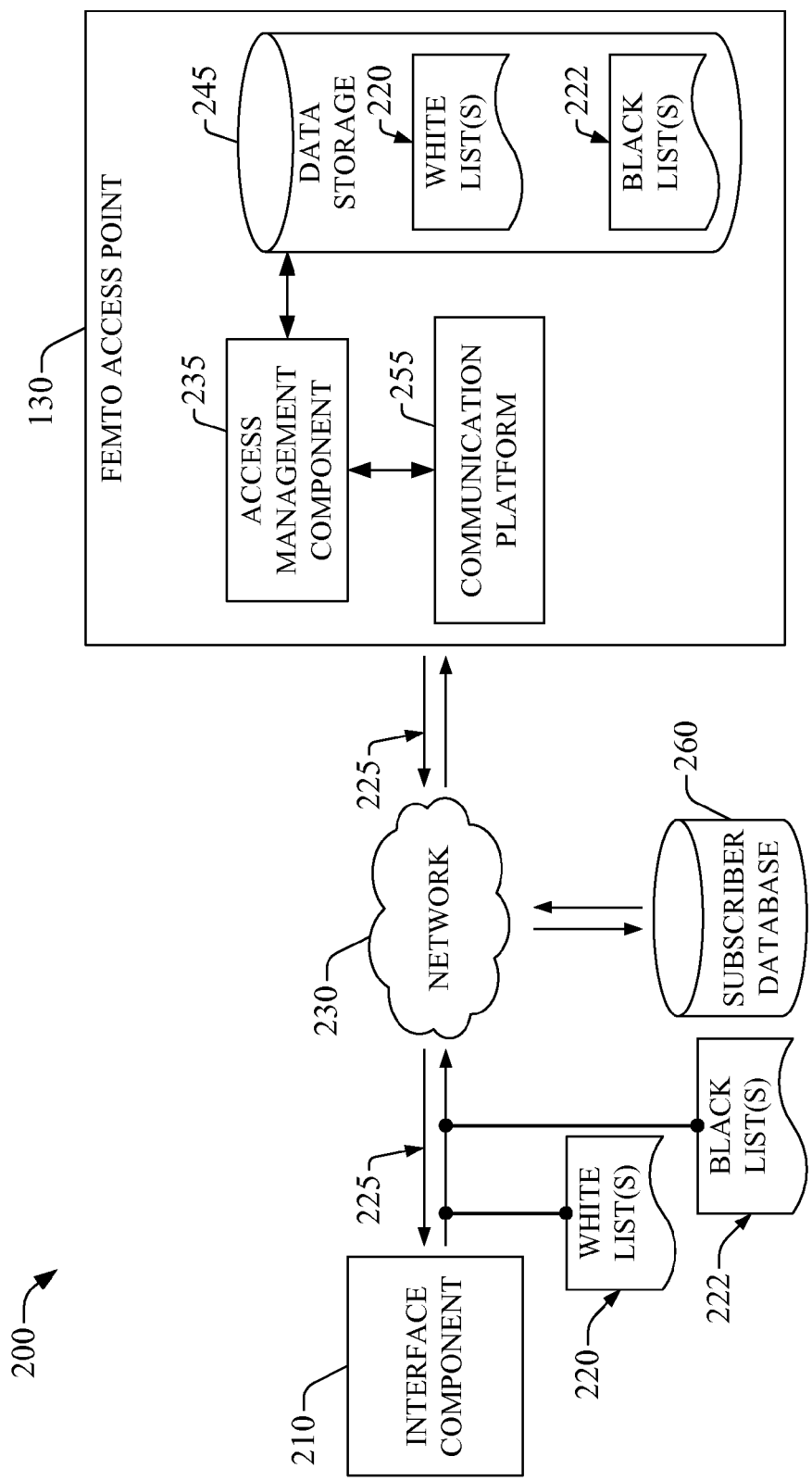
FIG. 2 is a block diagram of an example system that can facilitate selection of subscribers and/or subscriber stations to access coverage from a femtocell in accordance with an embodiment of the disclosed subject matter.

FIG. 2 is a block diagram of an example system 200 that can facilitate selection of subscribers and/or subscriber stations to access coverage from a femtocell in accordance with an embodiment of the disclosed subject matter. In an aspect, selection of subscribers and/or subscriber stations can enable or disable femtocell coverage for specific subscriber(s) or subscriber station(s). A means provided by example system 200 to facilitate authorizing, denying, revoking, and/or terminating access to specific subscribers, or subscriber station(s), comprises what is herein termed as a "White List(s)" (e.g., access control list(s))—an instrument that can facilitate management of access to femtocell coverage.

In example system 200, an interface component 210 can facilitate configuration, or set up, of a list(s) (e.g., white list 220, black list 222) of wireless mobile station numbers approved for coverage through femto access point 130. It is to be noted that substantially any identification token(s), label(s), or code(s) that can facilitate identifying a subscriber station can be employed to identify a subscriber station in a white list 220 or black list 222. In an aspect, a white list(s) 220 associated with femto AP 130 can include information related to subscriber stations and respectively associated subscribers that are granted respective levels of access to the femto AP 130 on a permanent or temporary basis. In another aspect, a black list(s) 222 associated with femto AP 130 can include information related to subscriber stations and respectively associated subscribers that are not granted access to the femto AP 130, where the opting out (e.g., refusal) or denial of coverage by the femto AP 130 can result in such subscriber stations being included on the black list(s) on a permanent or temporary basis.

In an aspect, the interface 210 can be networked (e.g., via a WAN, LAN, or backhaul pipe) with femto AP 130 and can convey white list(s) 220 and/or black list(s) 222 over network link(s) 225. In an aspect, interface component 210 can be a web-based, online graphic user interface (GUI), and/or other networked interfaces, which can facilitate entering or configuring a white list 220 or black list 222, can be employed, as desired, such as, for example, voice or sound commanded interface(s), touch commanded interface(s), biometric commanded interfaces(s), and the like. A communication platform 255 can facilitate reception of the white list(s) 220 and/or black list(s) 222 and can convey white list(s) 220 and/or black list(s) 222 to an access management component 235 that can exploit the white list(s) 220 and/or black list(s) 222 to facilitate managing access to coverage provided by femto AP 130 to subscriber stations and associated subscribers. White list(s) 220 and/or black list(s) 222 can be stored in the data storage 245 in the femto AP 130; and, as desired, white list(s) 220 and/or black list(s) 222 can be stored in disparate network components such as network component administered by a service operator. In addition, interface component 210 can access a subscriber database through network 230, in order to extract identification numbers, codes, tokens, or labels for subscribers/subscriber stations that can be entered in a white list 220 and/or black list 222.

In an illustrative, not-limiting aspect of the subject innovation, white list(s) 220 (or any set of numbers, codes or tokens thereon, that can comprise a set of subscriber stations (e.g., mobile phones) approved for coverage by femto AP 130) and/or black list(s) 222 (or any set of numbers, codes or tokens thereon, that can comprise a set of subscriber stations (e.g., mobile phones) not approved for coverage by femto AP 130) can be portable through accounts or billing groups associated with a set of subscribers to a service operator that can administer femto AP 130, or a macro network. As an illustration, white list(s) 220 and/or black list(s) 222 each can support up to N fields (N a positive integer; e.g., N=50) for unique mobile phone numbers (e.g., MSIDSNs), or any suitable identifying codes or tokens. The number N of fields can be determined, or configured, by a service operator based at least in part on technical aspects (e.g., network resources, quality of service consideration, macro area of coverage (e.g., MSA/RSA, . . . ) and commercial aspects (e.g., promotional considerations, mitigation of customer attrition, gains in market share, etc.) aspects of provision of coverage. As an example, N can be subscriber dependent or femto AP dependent.

In contrast to management of access authorization via femto AP 130, it should be appreciated that configuration of white list(s) 220 (e.g., registration authorization for femto coverage) and/or black list(s) 222 through a network mechanism(s) (e.g., interface component 210) can provide at least the following advantages. It is to be noted that the following advantages are illustrative and not limiting, as other advantages associated with white list(s) 220 and/or black list(s) 222, as are realized, are intended to lay within the scope of the innovation(s) described in the subject specification. (1) Access through a networked interface (e.g., online or otherwise) can reduce provisioning lead time and provides a means for customers to update and personalize a femto AP autonomously (e.g., free of interaction with technical support entities) at substantially any time. (2) Security against devices attempting to hack into the femto AP when networked with it, and support of extensible sharing/networking of the authorization scheme. (3) Networked interface (e.g., online or otherwise) can provide a superior, rich customer experience substantially free of requirement(s) to understand/interpret femto AP programming interface or configuration nomenclature. (4) End user(s) can manage (e.g., remove select covered numbers, or add additional numbers for coverage up to an allotted amount for white list(s) associated with the user. (5) Capacity to determined Quality of Service (QoS), grade of service, or service experience, for specific authorized subscribers. (6) Capacity to check for valid wireless device numbers, codes or tokens (e.g., MSISDNs); subscriber's active numbers, codes or tokens; and numbers, codes or tokens on service accounts in good standing; such capacity can be provided through networked access to a subscriber database 260.

White list(s) 220 and black list(s) 222 can facilitate management of access to coverage by a femto AP (e.g., femto AP 130) and services associated with the femto AP. Various illustrative aspects of innovation based at least in part on a white list concept also are discussed herein. It is to be noted, notwithstanding, that variations and extensions of such illustrative aspects can be realized and are within the scope of the subject innovation.

Figure 3:
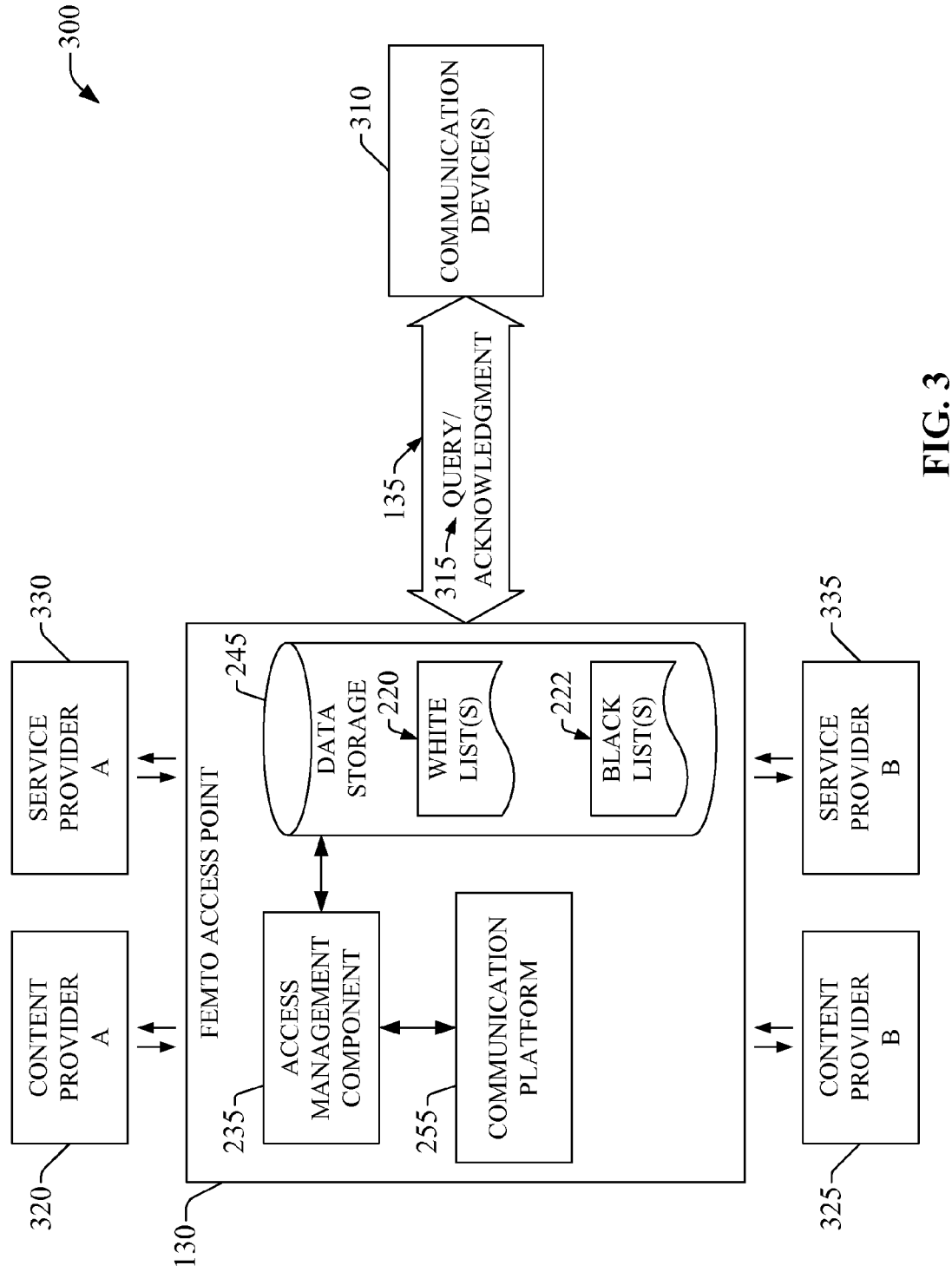
FIG. 3 is a block diagram of an example system that can interactively prompt communication devices to facilitate efficiently managing a white list(s) associated with a femto AP and management of access of communication devices to the femto AP in accordance with an aspect of the disclosed subject matter.

FIG. 3 is a block diagram of an example system 300 that can interactively prompt communication devices to facilitate efficiently managing a white list(s) associated with a femto AP and management of access of communication devices to the femto AP in accordance with an aspect of the disclosed subject matter. The example system 300 can facilitate sharing of content and/or provision of services between a communication device and the femto AP 130, which can employ broadband technology to facilitate sharing of content and/or provision of services at broadband data transmission rates, and/or other communication devices or other electronic devices (e.g., digital video player) that are connected to the femto AP 130. As a result, in example system 300, content can be shared and/or services can be provided to a communication device(s) via the femto AP 130 at a much faster transmission rate than can be realized in conventional systems (e.g., macro communication networks employing macro base stations) that support over-the-air data transmission rates that are significantly slower than broadband transmission rates.

In example system 300, the femto AP 130 (e.g., femtocell) can scan a frequency spectrum or band in which communication devices 310 can communicate to facilitate detecting communication devices 310 that are in the cell coverage area (e.g., area 125) of the femto AP 130. The femto AP 130 can automatically detect a communication device(s) 310 (e.g., subscriber station(s), such as a mobile phone) that enters the cell coverage area of the femto AP 130. In an aspect, the access management component 235 can facilitate automatically generating and transmitting a query 315, which can be transmitted by the communication platform 255, to the communication device(s) 310 via FL/RL 135 to prompt the communication device(s) 310 to connect (e.g., wirelessly connect) or request to connect (e.g., access) to the femto AP 130 to access content and/or services associated with the femto AP 130 and be entered on a white list(s) 220 associated with the femto AP 130. Interactively prompting detected communication devices 310 to opt in to the white list(s) 220 of the femto AP 130 and accessing content and/or services associated with the femto AP 130 can facilitate efficient population and management of the white list(s) 220 and management of access to the femto AP 130 and associated content and/or services. The communication device(s) 310 can communicate a response to the prompt or query 315 to accept the invitation to opt in to the white list(s) 220 and request access to the femto AP 130 or can refuse the prompt to opt in and access the femto AP 130. In another aspect, a communication device(s) 310 can enter the cell coverage area of the femto AP 130 and can convey a request or query 315 to facilitate accessing coverage of femto AP 130. Such a query 315 or request can be received by communication platform 255 via a FL/RL 135. For instance, the query 315 can be conveyed via an online GUI, an email message, a SMS message, MMS message, a voice mail, a web prompt, USSD (or * and # codes), and the like.

In another aspect, the access management component 235 can be configured to allow or reject the request for access by the communication device(s) 310, where allowance or rejection of a request can be based at least in part on various metrics (e.g., predefined access criteria), such as security, type of communication device, profile of the user (e.g., subscriber) that operates/operated the communication device 310 that requests access, historical information regarding the communication device 310 or associated user (e.g., abusive use of the femto AP 130 and associated services), available bandwidth, bandwidth requirements of the communication device, etc. Upon allowance of a request, the access management component 235 can query as to whether there is a slot(s) available to be filled in white list(s) 220 associated with accounts served by femto AP 130, and when a slot (e.g., space) is available in the white list(s) 220 for a subscriber station identifier number (e.g., MSISDN, IMSI), code or token, and/or other information related to the communication device 310, the query can further probe whether access to the femto AP 130 is to be granted on a permanent or temporary basis (e.g., to reduce risk exposure to security problems, maintain available space on white list(s) 220 for other communication devices 310, etc.). Characteristics of femto coverage allowance can be set or pre-set through the access management component 235. In one aspect, the access management component 235 can prompt (e.g. via a query) the communication device 310 to indicate whether the communication device 310 desires to be added to the white list(s) 220 on a permanent (or semi-permanent) basis or temporary basis.

In an aspect, the access management component 235 can automatically detect the type of communication device(s) 310, resources available on the communication device(s) 310, services that can be utilized by the communication device(s) 310, type of technologies (e.g., communication technologies) supported by the communication device(s), bandwidth requirements of the communication device(s) 310, etc., to facilitate determining the level of access to grant to the communication device 310, including the content and/or services to be included in the subset of content and/or services for which the communication device 310 is to be granted access. In still another aspect, the access management component 235 can facilitate automatically generating and transmitting a query to the communication device 310, where the query can prompt the communication device 310 and associated user to provide information regarding the type of access, type of content, and/or type of services desired by the communication device 310. The communication device 310 can respond to the query to provide information regarding the type of access (e.g., data service, voice service), type of content, and/or type of service(s) desired by the communication device 310 to the femto AP 130.

The access management component 235 can receive such information and can analyze the information to facilitate determining whether the desired type of access, type of content, and/or type of service(s) is currently available. If the desired type of access, type of content, and/or type of service(s) is not currently available, the access management component 235 can facilitate sending a message to the communication device 310 that can indicate that the desired type of access, type of content, and/or type of service(s) is not currently available and can prompt the communication device 310 to select another desired type of access, type of content, and/or type of service(s), if any. If a desired type of access, type of content, and/or type of service(s) is currently available (e.g., whether the initial selection or subsequent selection), the access management component 235 can determine the level of access and a subset of content and/or services to be granted to the communication device 310.

In accordance with yet another aspect, the communication device 310 also can analyze current and/or historical information regarding the communication device 310 and associated user in relation to the femto AP 130 (e.g., historical access and usage of the femto AP 130 by the communication device 130) and can infer a level of access and a subset of content and/or services desired by the communication device 310 and/or to be granted to the communication device 310. For example, the access management component 235 can retrieve historical information related to the communication device 310 from the white list(s) 220.

In another aspect, subsequent to allowance and examination of information related to relevant white list(s) 220, the access management component 235 can update the white list(s) 220, which can be stored in data storage 245, to reflect the approved request for femto coverage by the femto AP 130. It is to be noted that access and update of collected subscriber identifier numbers (e.g., MSISDN), codes or token, and/or other information related to the communication device 310, also can be effected through network-based white list database(s), as desired. The white list(s) 220 can be updated to include desired information regarding the communication device 310, where the information can include, for example, identifier numbers, codes, or token of the communication device 310, type of communication device 310, resources available on the communication device 310, services that can be utilized by the communication device 310, type of access granted and/or the subset of content and/or services associated with the femto AP 130 for which access is granted, type of technologies (e.g., communication technologies) supported by the communication device 310, bandwidth requirements of the communication device 310, bandwidth allocated to the communication device 310, QoS policy associated with the communication device 310, time the communication device 310 is entered on the white list(s) 220, and/or historical data (e.g., usage data related to use of the femto AP 130 by the communication device 310), etc.

In another aspect, the access management component 235 can grant access to a subset of content and/or services associated with the femto AP 130 to the approved communication device 310. The content and/or services contained in the subset of content and/or services can be determined based at least in part on predefined access criteria. In an aspect, the predefined access criteria can relate to, for example, information stored in a white list(s) associated with the femto AP 130, the level of access granted to the communication device 310, the content and/or services available from the femto AP 130, type of communication device 310, bandwidth available to be allocated to the communication device 310, services that can be utilized by the communication device 310, historical data associated with the communication device(s) 310 in relation to the femto AP 130, QoS, resources available on the communication device 310, type of technologies (e.g., communication technologies) supported by the communication device 310, type(s) of content(s) and/or service(s) requested by the communication device 310, etc.

In an aspect, the content and services can be respectively provided by content provider A 320, content provider B 325, service provider A 330, and service provider B 335, that each can be connected (e.g., via wired connection or wireless connection) to the femto AP 130. It is to be appreciated and understood that the number of content providers and service providers depicted in system 300 is an example number selected for clarity and brevity, and the subject innovation is not so limited, as, in system 300, there can be virtually any desired number of content providers and service providers (e.g., less than two content providers or service providers, two content providers or service providers, or more than two content providers or service providers).

In an aspect, the services that can be associated with and/or provided via the femto AP 130 and the associated service providers (e.g., service provider A 330, service provider B 335) can be as desired, and can include, for example, voice services (e.g., wireless mobile phone calls), data services (e.g., messaging, Internet access, . . . ), applications, electronic gaming, and/or access to content. The content that can be associated with and/or provided via the femto AP 130 and the associated content providers (e.g., content provider A 320, content provider B 325) can be as desired, and can include, for example, data content (e.g., word processing files), web content (e.g., web pages), audio content (e.g., MP3 files), video content (e.g., digital video of movies, television, music performances, etc.), multimedia content, digital images (e.g., photographs), etc. The content providers, content provider A 320 and content provider B 325, can be, or can be associated with, electronic devices, such as, for example, communication devices (e.g., cellular phone, smart phone, personal digital assistant (PDA), computer, . . . ), servers, digital video recorders/players, digital music recorders/players, analog video recorders/players (with digital conversion), analog music recorders/players (with digital conversion), electronic games, televisions, set-top boxes, cameras (e.g., digital cameras), and/or navigation systems or devices (e.g., global position satellite (GPS) system.

As an example of interactive white list prompting to facilitate sharing content or services, an owner of a femto AP 130 (e.g., femtocell) can have a digital video recorder/player connected to the femto AP 130, where a communication device 310 that is granted access to the digital video recorder/player can access content (e.g., audio content, such as a song file) contained in the digital video recorder/player. The femtocell owner has a friend who has a communication device (e.g., cellular phone), and the femtocell owner desires to share the content with the friend. Conventionally, downloading the content over-the-air via a macro base station can be inefficient as the data transmission rate can be significantly slower than the transmission rate for broadband communications. In accordance with the subject innovation, the friend of the femtocell owner can bring his communication device 310 into the femtocell coverage area, where the access management component 235 of the femto AP 130 can automatically detect the communication device 310 and can interactively and automatically prompt the communication device 310 to opt in to be added to the white list(s) 220 of the femto AP 130 and access the femto AP 130 and the desired content. The access management component 235 can grant access of the femto AP 130 and an associated subset of content and services (including access to the desired content) to the communication device 310 of the friend. The communication device 310 can access the desired content via the femto AP 130, where the desired content can be downloaded from the content provider (e.g., digital video recorder/player) to the friend's communication device 310 via the femto AP 130 at a data transmission rate for broadband. As a result, the desired content can be downloaded to the communication device 310 at significantly higher speed than in conventional systems.

In accordance with an aspect, the access management component 235 can monitor access of the femto AP 130 by communication devices 130 utilizing the femto AP 130 to facilitate efficiently managing access to the femto AP 130. For instance, when monitoring a communication device 310, if the access management component 235 observes that the communication device 310 has not been accessing content or a service(s) for which access was granted for a predefined period of time, the access management component 235 can facilitate automatically generating and transmitting a query to the communication device 310 to prompt the communication device 310 to indicate whether the communication device 310 desires to continue accessing the subset of content and/or services, or a portion thereof. The communication device 310 can provide a response to the query to indicate that the communication device 310 desires to continue accessing the subset of content and/or services, or portion thereof, or does not desire to continue accessing the subset of content and/or services. The access management component 310 can continue to grant access of the subset of content and/or services if the communication device 310 indicates that it desires to continue access to the subset of content and/or services, can terminate access of the subset of content and/or services by the communication device 310 if the communication device 310 indicates that it does not desire to continue access to the subset of content and/or services, or can modify the subset of content and/or services for which access is granted to the communication device 310 (e.g., if it is desired to discontinue access of a portion of the subset of content and/or services) and the white list(s) 220 can be updated to reflect the modification. When monitoring the communication device 310, if the access management component 235 observes that the communication device 310 is accessing the subset of content and/or services, the access management component 235 can allow the access to the subset of content and/or services to continue.

In another aspect, if the request for access by the communication device(s) 310 is rejected by the access management component 235 or the communication device 310 indicates that the communication device 310 desires to opt out of accessing the femto AP 130, or if the access management component 235 determines that there is no available slot in the femto AP 130 (and associated white list(s) 220), the access management component 235 can deny access of the femto AP 130 to the communication device 310. In still another aspect, when access is denied, the communication device 310 can be placed on a black list(s) 222 associated with the femto AP 130, on a permanent (or semi-permanent) or temporary basis, for example, by the access management component 235, where the black list(s) 222 can be stored in data storage 245. For instance, if the access management component 235 receives a message from the communication device 310 that indicates the communication device 310 desires to permanently (or semi-permanently) opt out of coverage by the femto AP 130 and/or if the access management component 235 determines that the communication device 310 is not to be granted access to coverage by the femto AP 130 on a permanent basis based at least in part on predefined access criteria, the access management component 235 can facilitate updating the black list(s) 222, and storing the black list(s) 222 in data storage 245, to include information related to the communication device 310, where the communication device 310 can be listed in the black list(s) 222 on a permanent (or semi-permanent) basis.

In yet another aspect, if the communication device 310 communicates a message to the femto AP 130 that indicates that the communication device 310 is opting out of coverage by the femto AP 130 at this time, but not on a permanent basis, or if access to the femto AP 130 is denied by the access management component 235 (e.g., due to no available slot on the white list(s)), the black list(s) 222 can be updated to include information related to the communication device 310 on the black list(s) 222 on a temporary basis, for example, by the access management component 235, where the black list(s) 222 can be stored in data storage 245. The communication device 310 can be removed from the black list(s) 222, as desired by the femto AP 130.

While on the black list(s) 222 (temporarily or permanently (or semi-permanently)), the communication device 310 is not eligible for access to or to attempt access to the femto AP 130. Employing black list(s) 222 can facilitate reducing signaling (e.g., unnecessary signaling) between communication devices and the femto AP 130, as it will be unnecessary for signaling by the femto AP 130 to a black-listed communication device with regard to the black-listed communication device accessing the femto AP 130; can facilitate reduced power consumption by the femto AP 130 and/or the black-listed communication device due in part to the reduced signaling; and can facilitate more efficient communication between the femto AP 130 and communication devices 310 in the coverage area of the femto AP 130, since unnecessary signaling can be reduced.

It is to be appreciated and understood that a request for access of the femto AP 130 can be effected by the femto AP 130 automatically, through an access management component (e.g., access management component 235), for example. Also, substantially any wireless communication device 310 within coverage area of femto AP 130 (e.g., area 125) can request access without intervention by a subscriber that operates femto AP 130, and who has previously entered a set of subscriber station numbers (e.g., MSISDNs), codes or tokens, via a networked interface (e.g., interface component 210). Alternatively, or in addition, a request for access can be prompted by a device utilized by a subscriber that operates the femto AP. Once a request is granted, a secure tunnel can be established from the device/client through the femtocell's IP connection or the default of the Radio Access Network if the IP connection is not available. Secure layers including utilizing the femtocell's VPN and/or USSD would ensure that the transaction is in fact secure.

In accordance with one embodiment of the subject innovation, the access management component 235 can utilize artificial intelligence (AI) methods to infer (e.g., reason and draw a conclusion based at least in part on a set of metrics, arguments, or known outcomes in controlled scenarios) regarding whether a communication device 310 is to be granted access to the femto AP 130 and associated content and/or services; a level of access to be granted to a communication device 310 with regard to the femtocell; a particular user of a communication device 310 (e.g., a particular user of a communication device 310 when the device has been utilized by more than one user at various times); a type of access, type of content, and/or type of service desired by a communication device 310; available functionality of a communication device 310; etc. Artificial intelligence techniques typically can apply advanced mathematical algorithms—e.g., decision trees, neural networks, regression analysis, principal component analysis (PCA) for feature and pattern extraction, cluster analysis, genetic algorithm, and reinforced learning—to historic and/or current data associated with system 300 to facilitate rendering an inference(s) related to the system 300.

In particular, the access management component 235 can employ one of numerous methodologies for learning from data and then drawing inferences from the models so constructed, e.g., Hidden Markov Models (HMMs) and related prototypical dependency models. General probabilistic graphical models, such as Dempster-Shafer networks and Bayesian networks like those created by structure search using a Bayesian model score or approximation can also be utilized. In addition, linear classifiers, such as support vector machines (SVMs), non-linear classifiers like methods referred to as "neural network" methodologies, fuzzy logic methodologies can also be employed. Moreover, game theoretic models (e.g., game trees, game matrices, pure and mixed strategies, utility algorithms, Nash equilibria, evolutionary game theory, etc.) and other approaches that perform data fusion, etc., can be exploited in accordance with implementing various automated aspects described herein. The foregoing methods can be applied to analysis of the historic and/or current data associated with system 300 to facilitate making inferences or determinations related to system 300.

Figure 4:
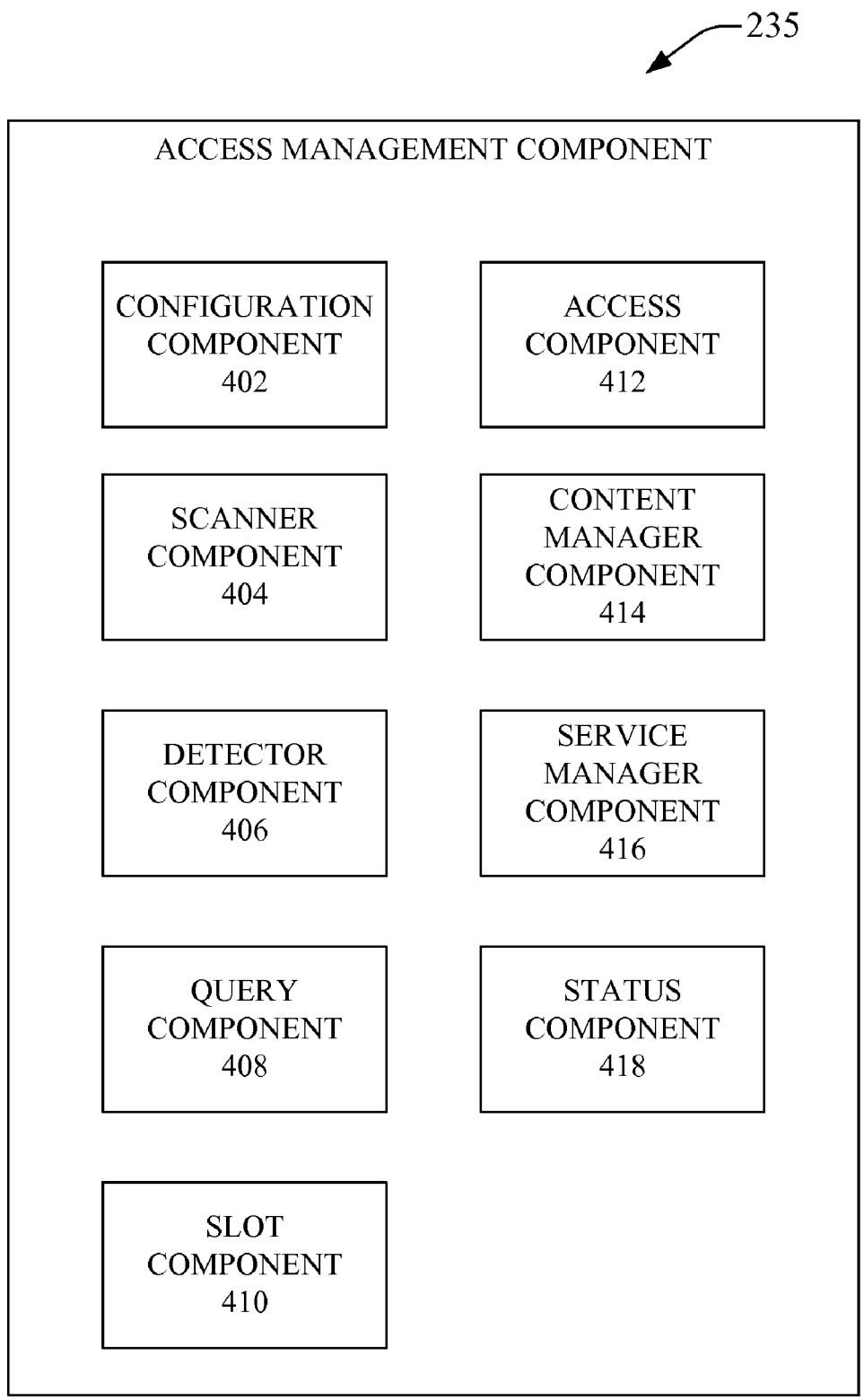
FIG. 4 is a block diagram an example access management component that can facilitate management of an access control list(s) and access of subscribers and subscriber stations to a femtocell in accordance with an aspect of the disclosed subject matter.

FIG. 4 depicts a block diagram of an example access management component 235 that can facilitate management of an access control list(s) (e.g., white list(s) 220) and access of subscribers and subscriber stations to a femtocell (e.g., femto AP 130) in accordance with an aspect of the disclosed subject matter. In an aspect, the access management component 235 can comprise a configuration component 402 that can facilitate generating, configuring, and/or updating a white list(s) 220 (e.g., an access control list(s)) and/or a black list(s) 222 associated with femto AP 130. The configuration component 402 can receive information associated with a communication device(s) (e.g., 310) that is or has been within the coverage area of the femto AP 130. The configuration component 402 can receive the information associated with the communication device(s) from the communication device or via an interface component (e.g., 210) and/or other networked interfaces (e.g., voice or sound commanded interface(s), touch commanded interface(s), biometric commanded interfaces(s), etc.). The received information can be utilized to generate, configure, and/or update a white list(s) 220 and/or black list(s) 222 based at least in part on the information related to the communication device(s), information already contained in a white list(s) and/or black list(s), predefined access criteria, and/or other information.

In another aspect, the access management component 235 can include a scanner component 404 that can scan a frequency spectrum in which communication devices can occupy and communicate to facilitate detecting communication devices 310 that enter the cell coverage area (e.g., area 125) of the femto AP 130. The access management component 235 also can include a detector component 406 that can detect communication devices 310 that enter the cell coverage area of the femto AP 130. The detector component 406 can facilitate identifying a particular communication device 310 based at least in part on detected or received information from the particular communication device 310. In another aspect, the detector component 406 also can monitor and detect whether a communication device 310 is accessing a subset of content and/or services for which access has been granted to facilitate managing access (e.g., allowing access to continue, modifying access, terminating access) of the subset of content and/or services by the communication device 310.

In another aspect, the access management component 235 can contain a query component 408 that can facilitate automatically generating queries, requests, or prompts for access (or continued access) to the femto AP 130 and associated content and/or services, and/or to provide other information (e.g., information related to the type of access, type of content, and/or type of service(s) desired) from the communication device 310, where the queries, requests, or prompts can be transmitted to communication devices 310 detected in the femto coverage area. The query component 408 also can receive queries and requests, such as a request to access the femto AP 130 and associated content and/or services, from communication devices 310 in the femto coverage area. In still another aspect, the access management component 235 can include a slot component 410 that can facilitate managing slots associated with the femto AP 130 (e.g., slot(s) in the white list(s) 220 and/or correspondingly in the femto AP 130) and determining availability of a slot associated with a femto AP 130 when a communication device desires to access the femto AP 130 and content and/or services associated therewith.

In yet another aspect, the access management component 235 can comprise an access component 412 that can facilitate controlling granting access of the femto AP 130 to a communication device 310 and granting access to a subset of content and/or services associated with the femto AP 130 to the communication device 310. The granting of access can be based at least in part on predefined access criteria associated with the femto AP 130.

In accordance with an aspect, the access management component 235 can comprise a content manager component 414 that can facilitate managing information related to, and access to, content associated with the femto AP 130. For instance, the content manager component 414 can create and maintain (e.g., update) a list of content that is available to be provided to a communication device(s) 310 which has been granted access. The list of content also can include other desired information, such as, for example, the location of the content in relation to the femto AP 130, the requirements (e.g., in relation to resources, technology capability, applications, . . . ) for accessing respective content. The access management component 235 can comprise a service manager component 416 that can facilitate managing information related to, and access to, services associated with the femto AP 130. For instance, the service manager component 416 can create and maintain (e.g., update) a list of services that are available to be provided to a communication device(s) 310 which has been granted access. The list of services also can include other desired information, such as, for example, the location of the services in relation to the femto AP 130, the requirements (e.g., in relation to resources, technology capability, applications, . . . ) for accessing respective services.

In another aspect, the access management component 235 can include a status component 418 that can facilitate determining whether a communication device 310 is to be stored in a white list(s) 220 or black list(s) 222 on a temporary basis or a permanent basis. The status component 418 also can facilitate monitoring or tracking the status of a communication device 310 that is accessing the femto AP 130 and/or associated services, and/or can monitor other components associated with the access management component 235 or femto AP 130. For example, the status component 418 can monitor whether a communication device 310, which is temporarily on the white list(s) 220, is still active in the cell coverage area of the femto AP 130. If the communication device 310 is no longer active in the cell coverage area (e.g., communication device 310 has left the cell coverage area, communication device 310 is turned off, ... ), the status component 418 can determine that the communication device 310 is to be removed from the white list(s) 220, and the configuration component 402 can update the white list(s) 220 to delete information related to the communication device 310 from the white list(s) 220.

In view of the example systems described herein, example methodologies that can be implemented in accordance with the disclosed subject matter can be better appreciated with reference to flowcharts in FIGS. 5-9. For purposes of simplicity of explanation, example methodologies disclosed herein are presented and described as a series of acts; however, it is to be understood and appreciated that the claimed subject matter is not limited by the order of acts, as some acts may occur in different orders and/or concurrently with other acts from that shown and described herein. For example, a methodology disclosed herein could alternatively be represented as a series of interrelated states or events, such as in a state diagram. Moreover, interaction diagram(s) may represent methodologies in accordance with the disclosed subject matter when disparate entities enact disparate portions of the methodologies. Furthermore, not all illustrated acts may be required to implement a methodology in accordance with the subject specification. It should be further appreciated that the methodologies disclosed throughout the subject specification are capable of being stored on an article of manufacture to facilitate transporting and transferring such methodologies to computers for execution by a processor or for storage in a memory.

Figure 5:
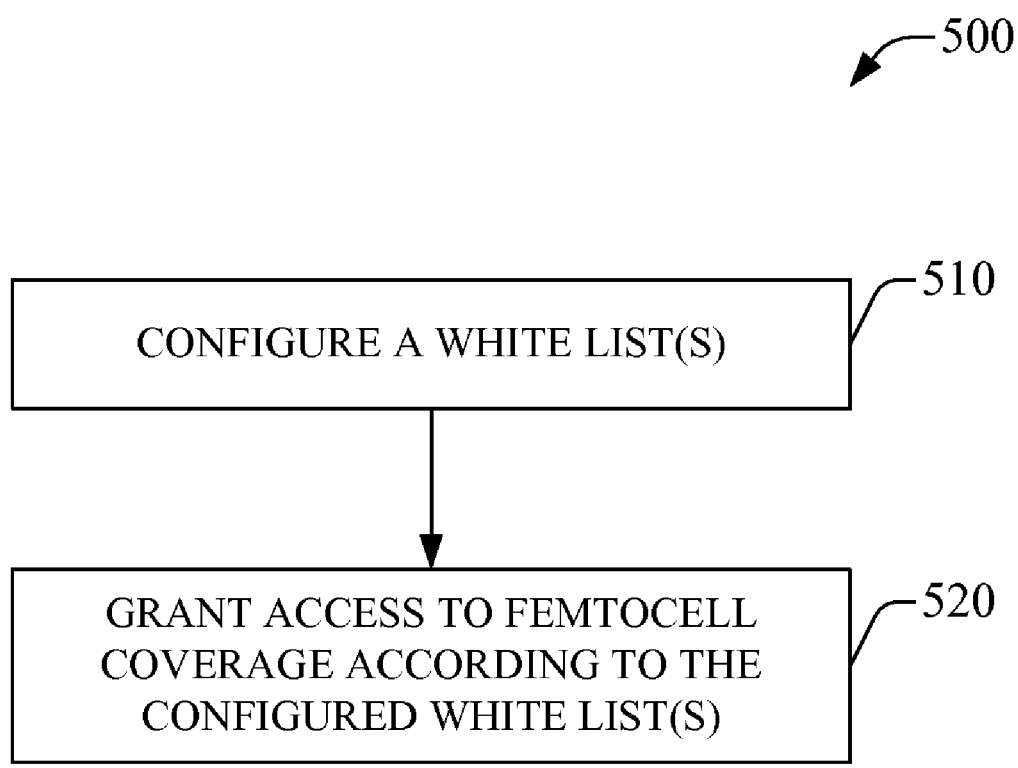
FIG. 5 illustrates a flowchart of an example methodology for managing access of subscribers and subscriber stations to cell coverage in accordance with an aspect of the disclosed subject matter.

FIG. 5 presents a flowchart of an example methodology 500 for managing access of subscribers and subscriber stations to cell (e.g., femtocell) coverage in accordance with an aspect of the disclosed subject matter. At 510, a white list(s) (e.g., access control list(s)) associated with a femtocell can be configured. In an aspect, configuration of the white list(s) (e.g., 220) can be performed via a networked interface, interactively or automatically based at least in part on operation conditions of the femtocell. The configuration of the white list(s) can relate to, for example, initial provisioning of the femtocell, capturing of wireless communication devices (e.g., 310), responding to request for access by a communication device, updating extant access control lists, and so forth. At 520, access to cell (e.g., femtocell) coverage can be granted at least in part according to the configured white list(s). In another aspect, the configured white list(s) can possess an associated profile that can facilitate controlling logic for utilization of the white list(s), via a set of parameters that can determine conditions of access to the femto AP 130 and associated subset of services, type of access to the femto AP 130 and associated subset of services, subset of services available to a particular communication device or associated user of communication device, etc.

Figure 6:
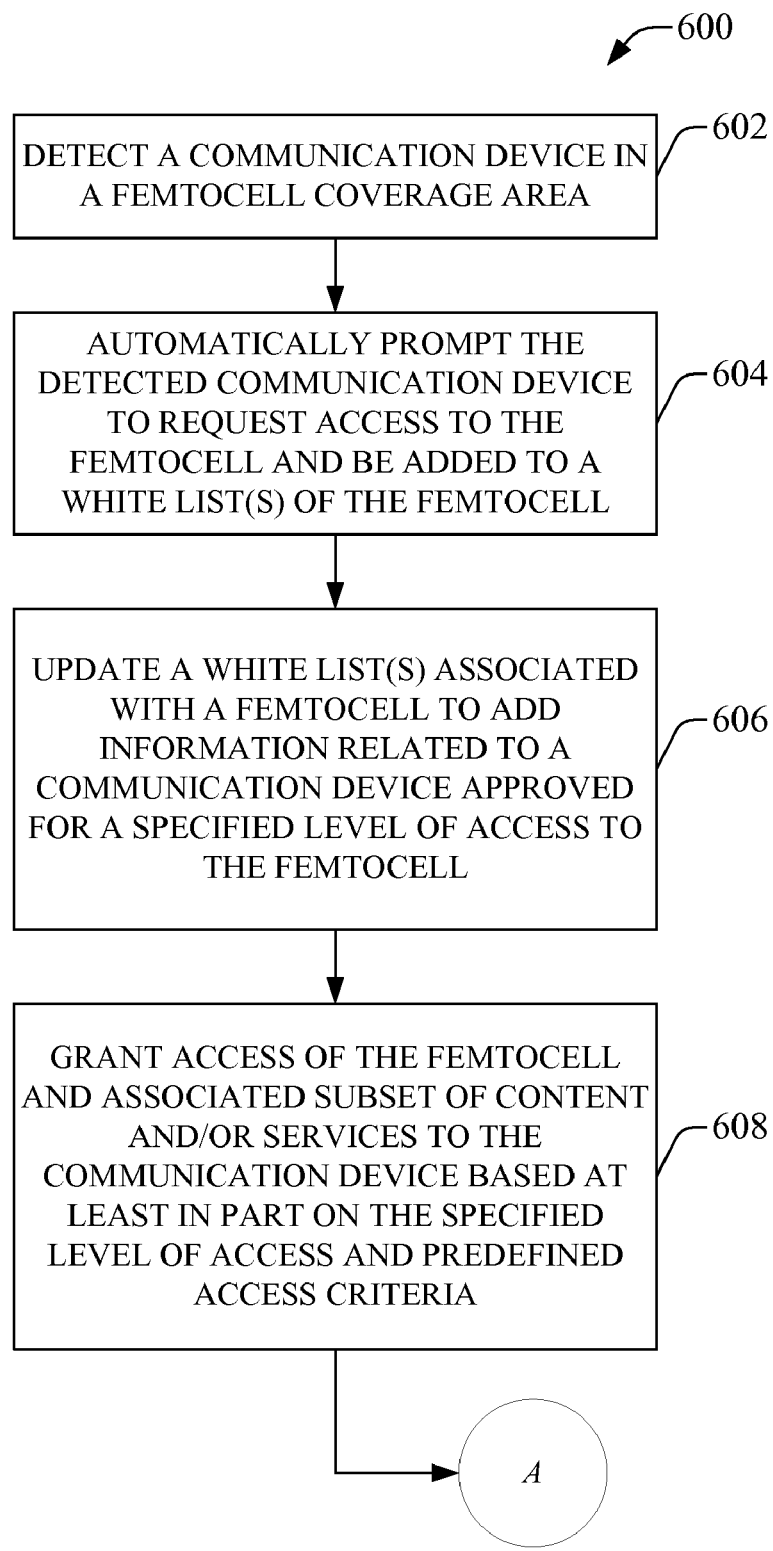
FIG. 6 illustrates a flowchart of an example methodology that can employ interactive white list prompting of a femtocell to facilitate managing access of subscribers and subscriber stations to femtocell coverage and associated content and services in accordance with an aspect of the disclosed subject matter.

FIG. 6 illustrates a flowchart of an example methodology 600 that can employ interactive white list (e.g., access control list) prompting of a femtocell (e.g., femto AP 130) to facilitate managing access of subscribers and subscriber stations (e.g., communication devices) to femtocell coverage and associated content and services in accordance with an aspect of the disclosed subject matter. At 602, a communication device (e.g., 310) can be detected in a femtocell coverage area of the femtocell. In an aspect, the femtocell (e.g., femto AP 130) can scan a frequency band in which communication devices communicate to facilitate detecting communication devices operating in the femtocell coverage area of the femtocell. In an aspect, the access management component 235 of the femtocell can detect and/or identify the communication device based at least in part on identification information (e.g., device number, code, or token such as MSISDN) associated with the communication device. The femtocell also can identify (e.g., automatically, via query) other information associated with the communication device, such as type of communication device, compatible communication technologies of the communication device, types of services that the communication device can or desires to utilize, etc.

At 604, the detected communication device can be automatically prompted to access (or request access) to the femtocell and be added to a white list(s) (e.g., 220) associated with the femtocell. In an aspect, the femtocell can automatically generate and transmit a query to the detected communication device to prompt the communication device to access or request to access the femtocell and content and/or services associated with the femtocell. In one aspect, the access management component 235 can facilitate automatically generating and transmitting the query to a detected communication device to facilitate automatically populating the white list(s) 220.

At 606, the white list(s) can be updated to include information related to the communication device approved for a specified level of access to the femtocell. In an aspect, when a communication device desires to opt in to access the femtocell and is approved to access the femtocell (e.g., when a slot is available on the white list(s) 220 and the communication device meets other predefined access criteria), the access management component 235 can facilitate updating the white list(s) 220 to store desired information (e.g., identification information, account information, communication device information, content and/or services that can be exploited by the communication device, content and/or services for which the communication device is granted access, user information, QoS, and/or bandwidth allocation, etc.) related to the communication device and/or associated user in the white list(s) 220, where the white list(s) 220 can be stored in data storage 245. Information related to the communication device can be stored in the white list(s) 220 on a permanent basis or temporary basis, as desired.

At 608, access to the femtocell and a subset of content and/or services associated with the femtocell can be granted to the communication device based at least in part on the specified level of access and predefined access criteria. In an aspect, the predefined access criteria can relate to, for example, information stored in a white list(s) 220 associated with the femtocell, the content and/or services available from the femto AP 130, type of communication device, bandwidth available to be allocated to the communication device, etc. At this point, methodology 600 can be at reference point A, where methodology 700 can proceed from reference point A to facilitate efficiently managing access of content and/or services associated with the femtocell.

Figure 7:
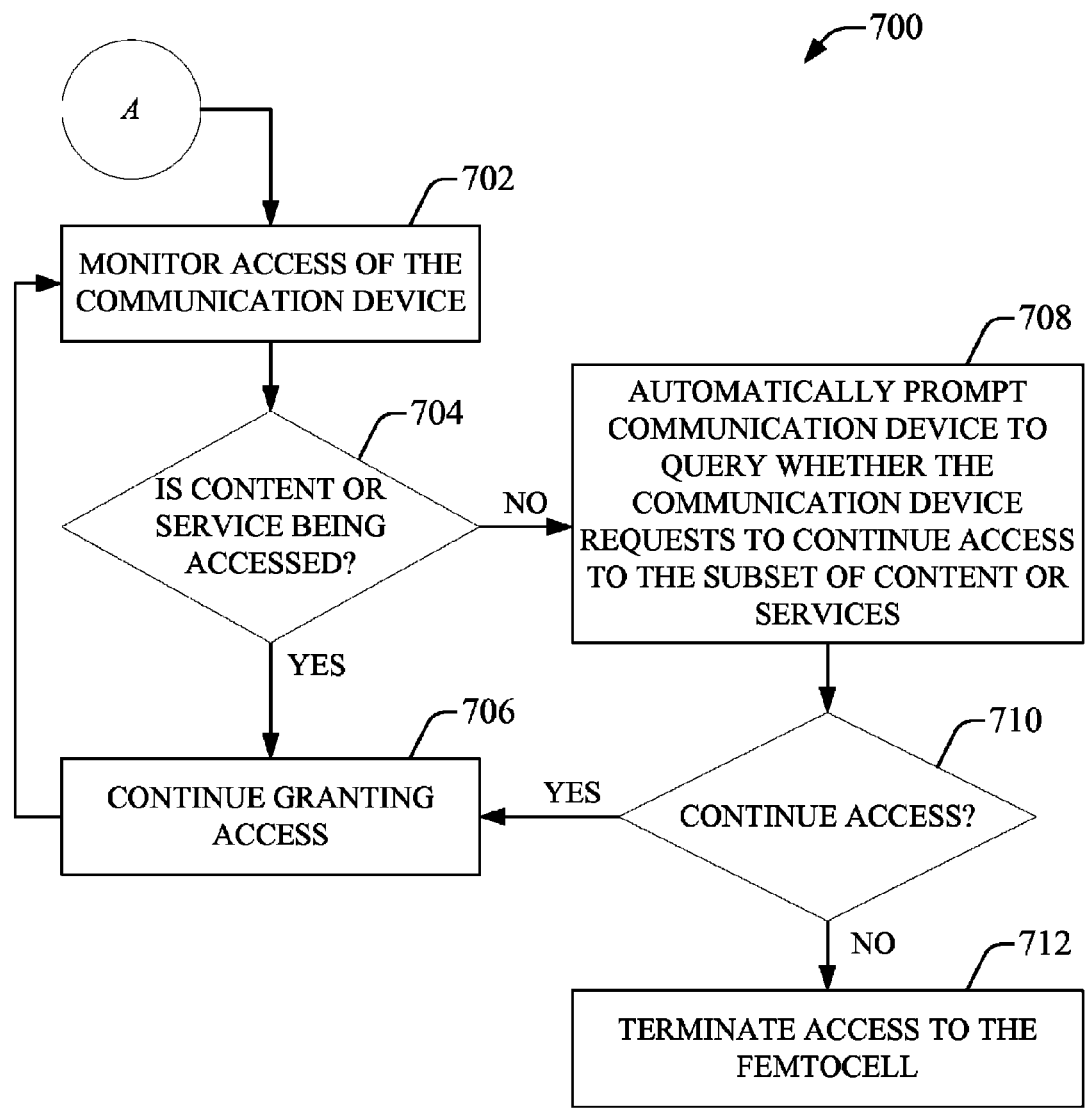
FIG. 7 illustrates a flowchart of an example methodology that can employ interactive white list prompting by a femtocell to facilitate efficiently managing access to content and/or services associated with the femtocell in accordance with an aspect of the disclosed subject matter.

FIG. 7 illustrates a flowchart of an example methodology 700 that can employ interactive white list prompting by a femtocell (e.g., femto AP 130) to facilitate efficiently managing access to content and/or services associated with the femtocell in accordance with an aspect of the disclosed subject matter. Methodology 700 can proceed from reference point A of methodology 600, where a communication device is granted access to a subset of content and/or services associated with the femtocell. At 702, access of the subset of content and/or services by the communication device (e.g., 310) can be monitored. In an aspect, an access management component 235 of the femtocell can monitor the activity of the communication device with regard to accessing the subset of content and/or services for which access has been granted to the communication device to facilitate determining whether the communication device is actually accessing or utilizing the subset of content and/or services.

At 704, a determination can be made regarding whether the communication device is accessing the subset of content and/or services. In an aspect, the access management component 235 receive information related to the activity of the communication device in relation to accessing the subset of content and/or services of the femtocell (e.g., the access management component 235 can monitor the activity to facilitate receiving the information related to the activity). If it is determined that the communication device is accessing or utilizing the subset of content and/or services, at 706, access to the subset of content and/or services can continue to be granted to the communication device. At this point, methodology 700 can return to reference numeral 702, where the activity of the communication device in relation to accessing the subset of content and/or services can continue to be monitored, and methodology 700 can proceed from that point.

If, at 704, it is determined that the communication device has not been accessing or utilizing the subset of content and/or services, or a portion thereof, (e.g., for a predefined period of time), at 708, a prompt can be automatically transmitted to the communication device to query whether the communication device requests to continue access to the subset of content and/or services of the femtocell. In an aspect, the access management component 235 can facilitate generating and transmitting a query to the communication device to prompt the communication device with regard to whether the communication device desires to continue accessing the subset of content and/or services.

At 710, a determination can be made regarding whether the communication device can continue to access (or at least is approved to access) the subset of content and/or services. The access management component 235 can receive information from the communication device that can indicate whether the communication device desires to continue accessing (or at least continue to be approved to access) the subset of content and/or services. Based at least in part on the received information, the access management component 235 can determine whether to continue to grant access to the subset of content and/or services to the communication device. If it is determined that the communication device can continue (e.g., desires to continue) to access the subset of content and/or services, methodology 700 can proceed to reference numeral 706, where access to the subset of content and/or services can continue to be granted to the communication device, and methodology 700 can proceed from that point.

If, at 710, it is determined that the communication device is not to continue to access the subset of content and/or services, at 712, access to the subset of content and/or services by the communication device can be terminated. For example, if the access management component 235 receives information from the communication device indicating that the communication device no longer desires to access the subset of content and/or services, or otherwise determines that access to the subset of content and/or services by the communication device is to be discontinued, the access management component 235 can facilitate terminating access of the subset of content and/or services by the communication device. In another aspect, the white list(s) 220 of the femtocell can be updated to reflect that access of the subset of content and/or services by the communication device is terminated or, if information related to the communication device is stored in the white list(s) 220 on a temporary basis, the white list(s) 220 can be updated to delete information related to the communication device from the white list(s) 220, as desired.

Figure 8:
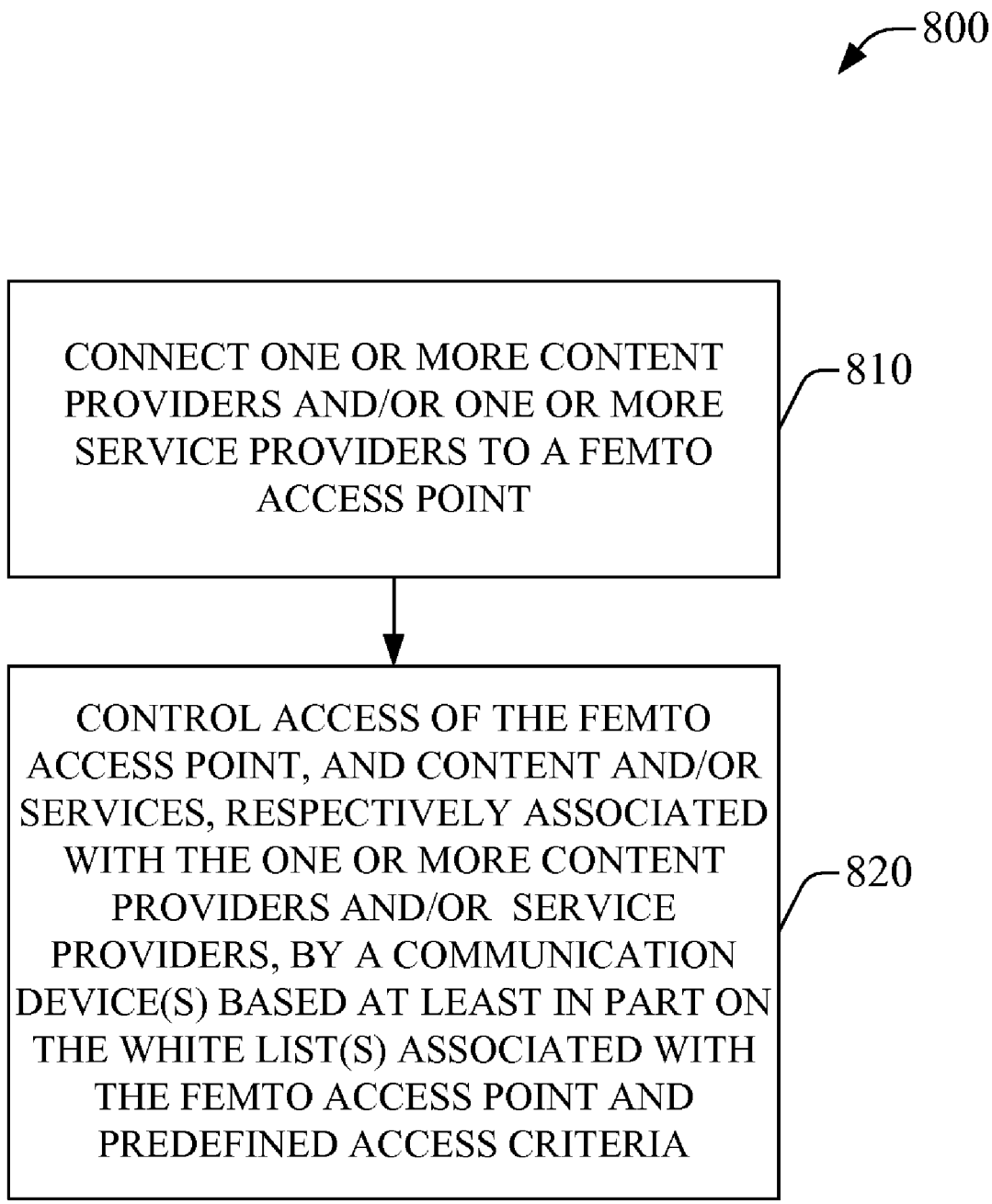
FIG. 8 depicts a flowchart of an example methodology that can connect content providers and service providers to a femto access point to facilitate sharing content and/or services in accordance with an aspect of the disclosed subject matter.

FIG. 8 depicts a flowchart of an example methodology 800 that can connect content providers and service providers to a femto access point (e.g., femto AP 130) to facilitate sharing content and/or services in accordance with an aspect of the disclosed subject matter. At 802, one or more content providers and/or one or more service providers can be connected (e.g., via wired connection or wireless connection) to a femto AP. In an aspect, the one or more content providers can comprise electronic devices, which can store and/or provide content, and are owned or operated by the owner or operator of the femto AP 130 and/or third-party content providers; and the one or more service providers can comprise services provided by the owner or operator of the femto AP 130 and/or third-party service providers. For example, a content provider can be an electronic device, such as a digital video recorder/player or a cellular phone, of the owner or operator of the femto AP 130 or a communication device (e.g., cellular phone, laptop computer) of a subscriber connected to the femto AP 130 (e.g., where the subscriber has agreed to allow access to the content stored on the subscriber's communication device).

The content providers can comprise electronic devices, such as, for example, computers, servers, cellular phones, smart phones, personal digital assistants (PDAs), digital video recorders/players, digital music recorders/players, analog video recorders/players (with digital conversion), analog music recorders/players (with analog conversion), electronic games, televisions, set-top boxes, cameras (e.g., digital cameras), and/or navigation systems or devices (e.g., global position satellite (GPS) system. The services provided can comprise, for example, voice services (e.g., wireless mobile phone calls), data services (e.g., messaging, Internet access, . . . ), access to applications, electronic gaming, and/or access to content (e.g., audio content, video content, multimedia content, . . . ).

At 804, access to the content and/or services, respectively associated with the content providers and service providers, by communication devices can be controlled based at least in part on the white list(s) 220 of the femto AP 130 and predefined access criteria. In an aspect, the access management component 235 can utilize information stored in the white list(s) 220 of the femto AP 130 to facilitate controlling access to content and/or services associated with the femto AP 130 by communication devices (e.g., 310).

Figure 9:
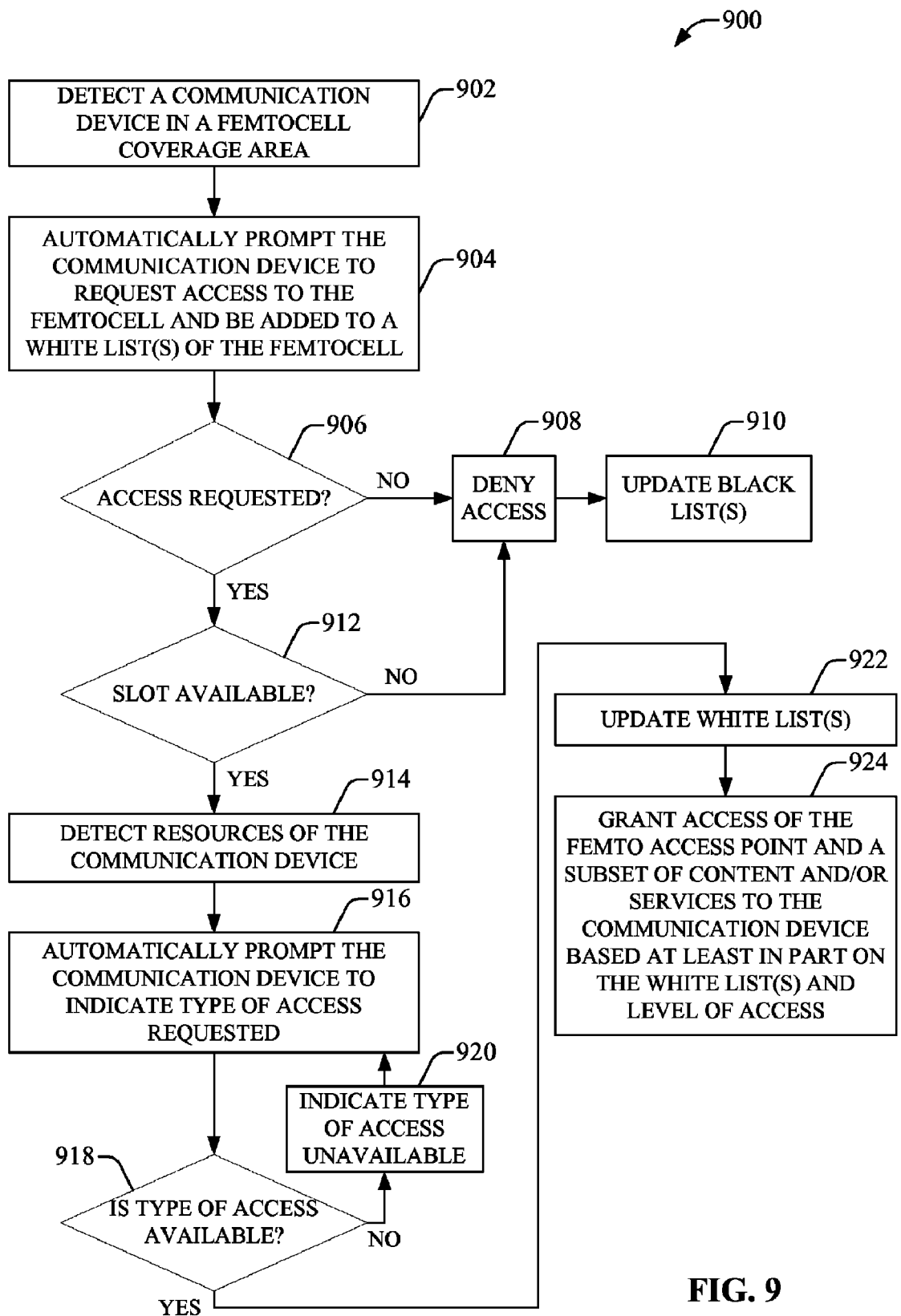
FIG. 9 depicts a flowchart of an example methodology that can employ interactive prompting to facilitate efficiently managing access of communication devices to femtocell coverage in accordance with an aspect of the disclosed subject matter.

FIG. 9 depicts a flowchart of an example methodology 900 that can employ interactive prompting to facilitate efficiently managing access of communication devices (e.g., 310) to femtocell coverage in accordance with an aspect of the disclosed subject matter. At 902, a communication device (e.g., 310) can be detected in a femtocell coverage area of the femtocell. In an aspect, the femtocell (e.g., femto AP 130) can scan a frequency spectrum or band in which communication devices communicate to facilitate detecting communication devices operating in the femtocell coverage area of the femtocell. In an aspect, the access management component 235 of the femtocell can detect and/or identify the communication device based at least in part on identification information (e.g., device number, code, or token such as MSISDN) associated with the communication device. The femtocell also can identify (e.g., automatically, via query) other information associated with the communication device, such as type of communication device, compatible communication technologies of the communication device, types of services that the communication device can or desires to utilize, etc.

At 904, the detected communication device can be automatically prompted to access (or request access) to the femtocell and be added to a white list(s) (e.g., 220) associated with the femtocell. In an aspect, the femtocell can automatically generate and transmit a query to the detected communication device to prompt the communication device to access or request to access the femtocell and content and/or services associated with the femtocell. In one aspect, the access management component 235 can facilitate automatically generating and transmitting the query to a detected communication device to facilitate automatically populating the white list(s) 220.

At 906, a determination can be made regarding whether the communication device is requesting access to the femtocell and associated content and/or services. In an aspect, the access management component 235 of the femtocell can facilitate determining whether the communication device is requesting access to the femtocell based at least in part on information received by the femtocell from the communication device that indicates the communication device desires to opt in and access the femtocell or indicates the communication device refuses to opt in to access the femtocell.

If it is determined that the communication device has refused access to the femtocell, at 908, access to the communication device can be denied. At 910, a black list(s) 222 associated with the femtocell can be updated to include information related to the communication device, where the black list(s) 222 can be utilized by the access management component 235 to facilitate reducing unnecessary signaling (e.g., prompting the communication device to access the femtocell) between the femtocell and the communication device, which can facilitate reducing power consumption by the femtocell and communication device and facilitate more efficient communication between the femtocell and other communication devices disposed in the femtocell coverage area.

If, at 906, it is determined that the communication device has accepted the prompt (e.g., opted in) to access the femtocell, at 912, a determination can be made regarding whether there is a slot available on the white list(s) 220 of the femtocell (and a slot available on the femtocell to which the communication device can be connected). For instance, the access management component 235 can query as to whether a slot is available in the white list(s) 220. If it is determined that there is no slot available, methodology 900 can proceed to reference numeral 908, where access of the femtocell by the communication device can be denied, and methodology 900 can proceed from that point.

If, at 912, it is determined that a slot is available on the white list(s) 220 (and a slot is available on the femtocell), at 914, resources associated with the communication device can be detected. For instance, the access management component 235 can facilitate detecting and determining the resources (e.g., voice services or capabilities, data services or capabilities, available applications, etc.) of the communication device. For example, the access management component 235 can detect that a particular cellular phone is a 3G phone that can utilize or exploit a particular subset of services and/or content associated with the femtocell, which can facilitate determining the type of access to be granted to the phone, the amount of bandwidth to allocate to the phone, and/or the subset of content and/or services that can be granted to the phone.

At 916, the communication device can be automatically prompted to indicate the type of access requested by the communication device. In an aspect, the access management component 235 can facilitate automatically generating and transmitting the prompt, which can inquire as to the type of access (e.g., voice service, data service, access to content, access to a service, . . . ) desired by the communication device, to the communication device. The communication device can transmit information indicating the type of access requested to the femtocell, where the access management component 235 can evaluate the received information.

At 918, a determination can be made regarding whether the requested type of access is available. In an aspect, the access management component 235 can determine whether the desired type of access requested by the communication device is available. If it is determined that the requested type of service is not available, at 920, a message that indicates the requested type of access is not available can be transmitted to the communication device. Methodology 900 can return to reference numeral 916, where the communication device can be automatically prompted to request another type of access, and methodology 900 can proceed from that point.

If, at 918, it is determined that the requested type of access is available, at 922, the white list(s) can be updated to include information related to the communication device and/or associated user. In an aspect, the access management component 235 can facilitate updating the white list(s) 220 to store desired information (e.g., identification information, account information, communication device information, type of femtocell access requested, content and/or services that can be exploited by the communication device, content and/or services for which the communication device is granted access, user information, QoS, and/or bandwidth allocation, etc.) related to the communication device and/or associated user in the white list(s) 220, where the white list(s) 220 can be stored in data storage 245.

Figure 10:
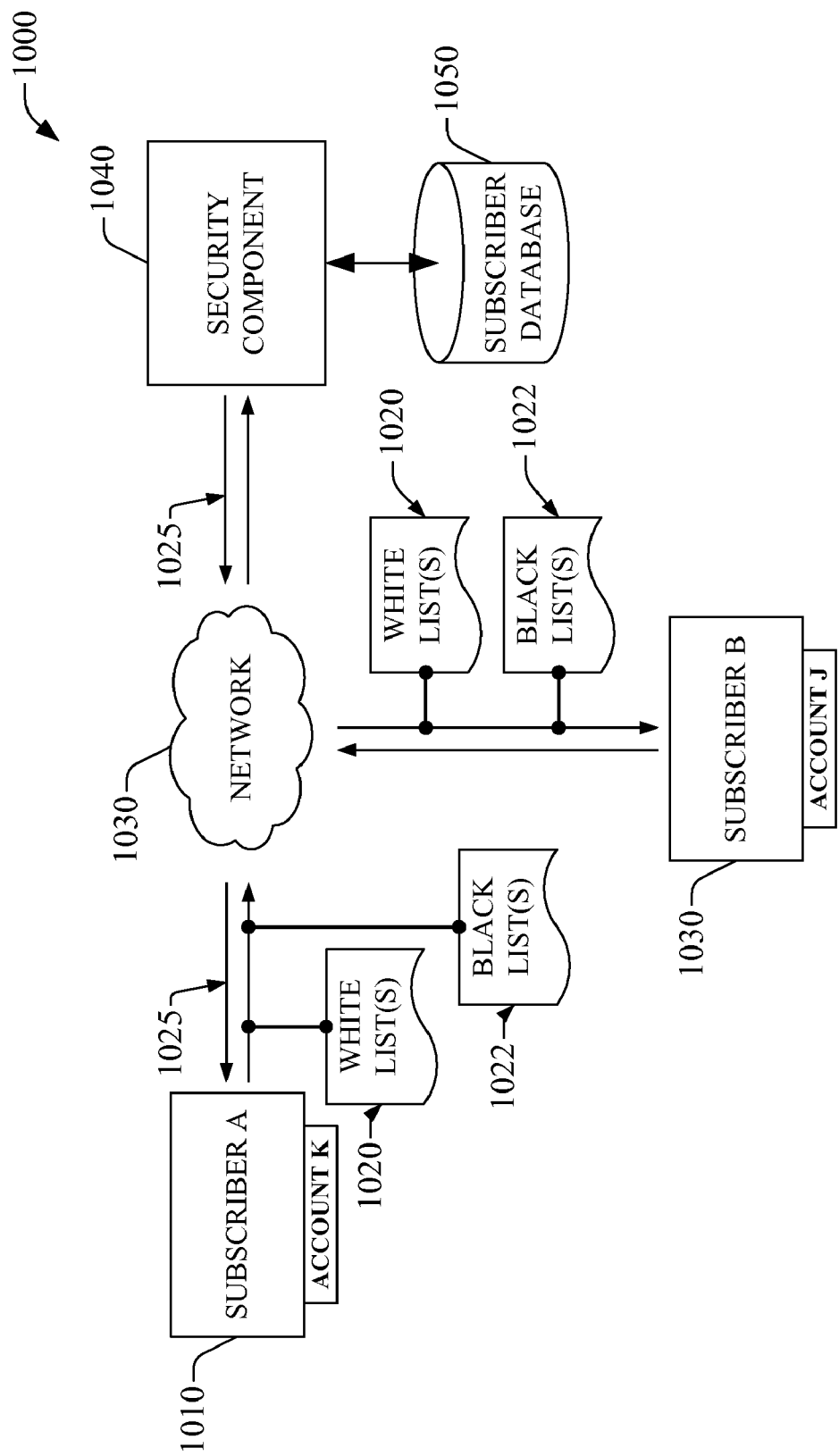
FIG. 10 is a block diagram of an example system that can facilitate sharing white list(s) and/or black list(s) among subscribers of a wireless network service in order to provide straightforward access configuration to, and activation of, a femtocell among femtocell subscribers.

At 924, the communication device can be granted access to the femtocell and a subset of content and/or services associated with the femtocell based at least in part on the white list(s) 220 and the level of access granted. In an aspect, the access management component 235 can facilitate granting access to a subset of services associated with the femto AP 130 to the communication device based at least in part on the white list(s), the level of femtocell access granted to the communication device (e.g., with regard to content and/or services associated with the femtocell), the user of the communication device, the type of communication device, available bandwidth of the femtocell, and/or other predefined access criteria. For example, an owner of the femtocell can desire to limit access of a communication device of the owner's child to a specified subset of content and services that is suitable for children. As another example, the owner of the femtocell can desire to limit access to certain content or services, and not allow access to other content or services, for a communication device due to current bandwidth availability. In still another example, the owner of the femtocell can desire to allow access to a first subset of content and/or services to the femtocell owner and other trusted or desired entities (e.g., spouse, friends, . . . ) and allow access to a disparate subset of content and/or services to other entities (e.g., visitors) to which access is granted, where the first subset of content and/or services can contain more content and/or services than the disparate subset of content and/or services. The user of the communication device can utilize the subset of content and/or services associated with the femtocell to which access is granted FIG. 10 is a block diagram of an example system 1000 that can facilitate sharing white list(s) (e.g., access control list(s)) and/or black list(s) among subscribers of a wireless network service in order to provide straightforward access configuration to, and activation of, a femtocell (e.g., femto AP 130) among femtocell subscribers. Subscribers can belong to disparate or same service accounts with either a macro service provider or femto provider, or both. For example, subscribers that share white list(s) 1020 and/or black list(s) 1022 can pertain to a group or family associated with a single service account. In example system 1000, subscriber A 1010 who belongs to account K can convey white list(s) 1020 and/or black list(s) 1022 over network 1030, via a wired or wireless link 1025, to subscriber B 1030 who belongs to account J. Subscriber A 1010 can hide or eliminate specific subscriber station numbers from white list(s) 1020 and/or black list(s) 1022 he/she/it grants to other subscribers. It should be appreciated that the granting of subscriber station numbers, codes or tokens can substantially reduce the amount of time to configure, or set up a white list(s) 1020 and/or black list(s) 1022, as opposed to manually re-entering multiple numbers, codes, or tokens (e.g., up to 50 numbers, codes or tokens) across multiple femtocells.

A security component 1040, or authorization layer, can facilitate ensuring that unauthorized mobile subscriber numbers, codes or tokens, respectively associated with communication devices (e.g., 310) are not provided when not approved by end users. Such approval can be determined via a specified privacy policy associated with the end user, or subscriber, which can be stored in a subscriber database 1050; the specified privacy policy can be configured/updated through various means, such as, for example, web-based interfaces, call center, text-message center, etc. Security component 1040 can ensure privacy integrity when white list(s) 1020 and/or black list(s) 1022 are shared among subscribers of different accounts (e.g., J≠K). In an illustrative aspect, security component 1040 can solicit subscribers outside a "white-list share" (or "black-list share") originating account to grant the authority for their subscriber station identifier number, code or token to be shared through white list(s) 1020 (or black list(s) 1022). To the latter end, security component 1040 can resort to various mechanisms that can include, but are not limited to including, a short message service (SMS) communication, a multimedia message service (MMS) communication, email, voice mail, web pop up, etc. Alternatively, or in addition, security component 1040 can mitigate security mechanism(s) complexity through validation via subscriber account information (e.g., stored in subscriber database 1050) in order to grant automatic access to a white list(s) 1020 and/or black list(s) 1022 within groups or families underneath a single service account, without additional security verification.

Figure 11:
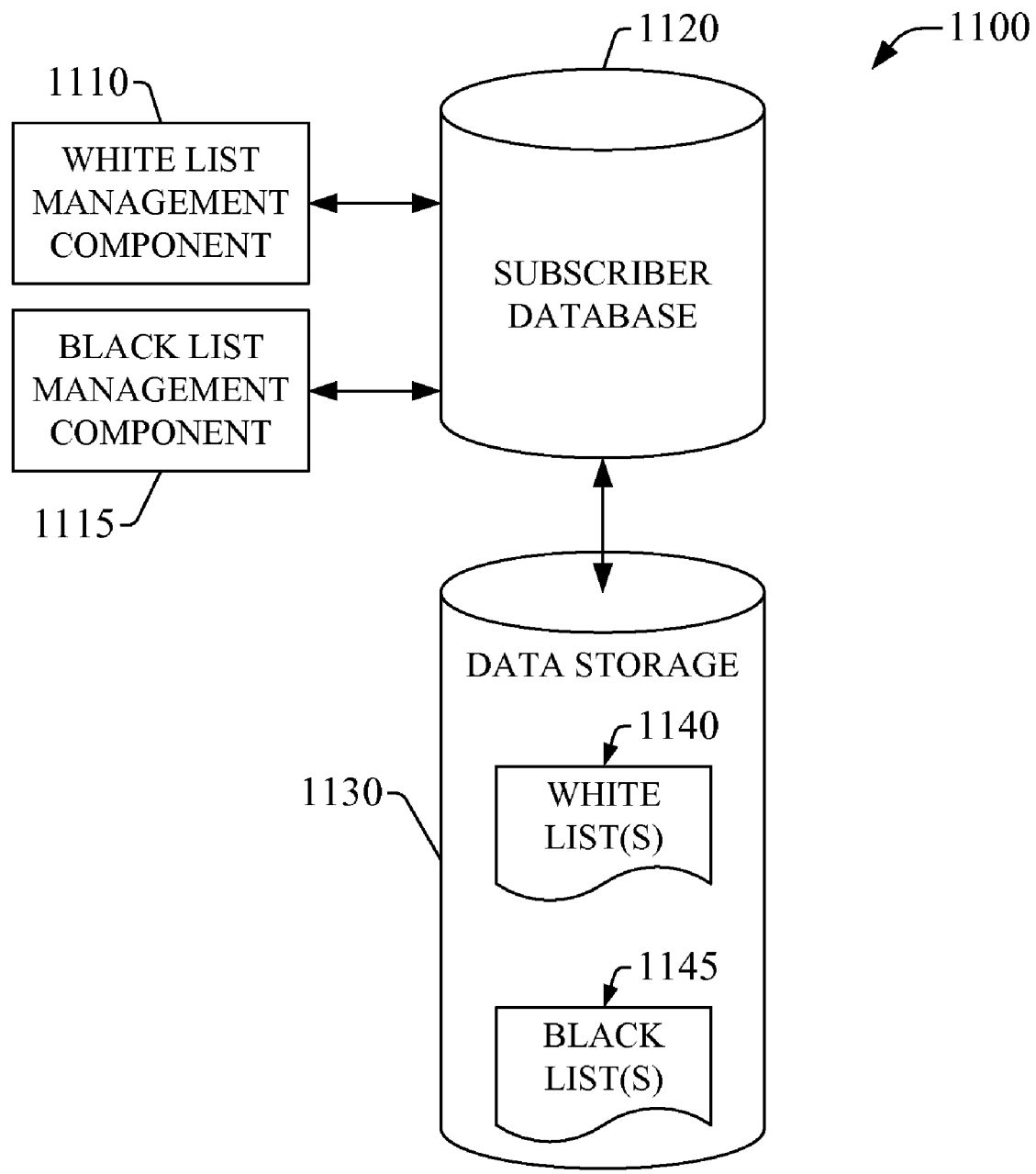
FIG. 11 is a block diagram of an example system that can facilitate management of a white list(s) and a black list(s) associated with a femtocell in accordance with an aspect of the disclosed subject matter.

FIG. 11 is a block diagram of an example system 1100 that can facilitate management of a white list(s) (e.g., an access control list(s)) and a black list(s) associated with a femtocell (e.g., femto AP 130) in accordance with an aspect of the disclosed subject matter. System 1100 can comprise a white list management component 1110 that can access a subscriber database 1120 which can be maintained by a service operator for femto and macro cells, and a data storage 1130 that retains a set of white lists 1140 associated with serviced subscribers, to associate white-listed subscribers across disparate white lists. Such association can lead to genesis of white-lists trees. In an aspect, the white list management component 1110 can implement mechanisms to facilitate mitigating exponential data growth and efficient storage of white-list trees like data-compression (e.g., wavelet, efficient tree representation, and so on), distributed data warehouses, and so forth.

In another aspect, system 1100 can comprise a black list management component 1115 can access a subscriber database 1120 which can be maintained by a service operator for femto and macro cells, and a data storage 1130 that can retain a set of black lists 1145 associated with serviced subscribers, to associate black-listed subscribers across disparate black lists. Such association can lead to genesis of black-lists trees. In an aspect, the black list management component 1115 can implement mechanisms to facilitate mitigating exponential data growth and efficient storage of black-list trees like data-compression (e.g., wavelet, efficient tree representation, and so on), distributed data warehouses, etc.

In still another aspect, the white list management component 1110 can deploy a white-list tree in accordance to the following illustrative, non-limiting scenario. (i) User 1 adds User 2 to his/her white list (e.g., 1140). (ii) User 2 adds User 3 to his/her white list (e.g., 1140). (iii) User 1 and User 3 can be associated through the respective white lists. (iv) User 1 and User 3 can match User 4 extant on each other's white lists. (v) User 1 and User 3 can associate User 5 that is on User 4's white list. White list management component 1110 can effect associations and manage generated white-list tree(s). It should be appreciated that substantially any association, hierarchical or non-hierarchical, or deployment of white lists 1140 can be implemented by the white list management component 1110 through information stored in subscriber database 1120 and data storage 1030. It is to be appreciated and understood that the black list management component 1115 similarly can deploy a black-list tree in accordance with the above illustrative, non-limiting scenario.

An illustrative, non-limiting, advantage of structured, hierarchical generation of white lists to subscribers (e.g., subscriber A 1010) is that more subscribers can have access to femtocells (e.g., femto APs 130) to gain coverage enhancement, or have access to added value through virtually unlimited usage on any femtocell or unique content and/or services available via a set of femtocells.

In addition, example system 1100 can track subscriber station identifier numbers (e.g., MSISDNs), codes or tokens, associated with white list(s) on record with a femto service provider. White list management component 1110 can validate white list(s) 1140, stored in data storage 1130, against current accounts and associated subscriber station identifier numbers (e.g., MSISDNs), codes, or tokens, for a service provider. In particular, when a subscriber, or end user, cancels an account with a service provider, white list(s) 1140 can be updated according to information retrieved from subscriber database 1120, or substantially any other database available to a service provider that contains information on service subscribers. In addition, when an end user changes their mobile or subscriber station number, code or token, (e.g., after relocation to a new area code, or the like) substantially all white list(s) 1140 that the mobile or subscriber station number, code or token is associated with can automatically be updated by the white list management component 1110.

An illustrative advantage of such automatic update of white list(s) 1140 is ease of use for end users to maintain current white list(s) 1140 without a need to keep track of each subscriber station number, code or token associated with the white list(s) 140. In addition, updated white list(s) 1140 can maintain the value proposition of the femtocells for end users and service operator by a seamless move of traffic off of the macro network (e.g., a WAN) to femto network(s).

In accordance with an embodiment, the white list management component 1110 can facilitate distinguishing between communication devices (and associated users) that are temporarily on a white list 1140 of a subscriber as compared to communication devices (and associated users) that are permanently on the white list 1140 of the subscriber when a white list 1140, or subset thereof, of one subscriber is added to a white list 1140 of another subscriber. For instance, the white list management component 1110 can facilitate selecting or associating subscribers that are permanently on a white list 1140 of one subscriber, but not selecting or associating subscribers that are temporarily on the white list 1140 of the one subscriber, and adding a subset of the white list of the one subscriber (e.g., the selected or associated subscribers that are permanently on the white list) to the white list 1140 of the other subscriber. It is to be appreciated and understood that the black list management component 1115 similarly can select a desired subset of subscribers on one black list 1145 of one subscriber (e.g., selecting subscribers that are permanently on a black list of the one subscriber, but not subscribers that are temporarily on the black list of the one subscriber) and adding the subset of subscribers to the black list 1145 of another subscriber when in accordance with the embodiment.

Figure 12:
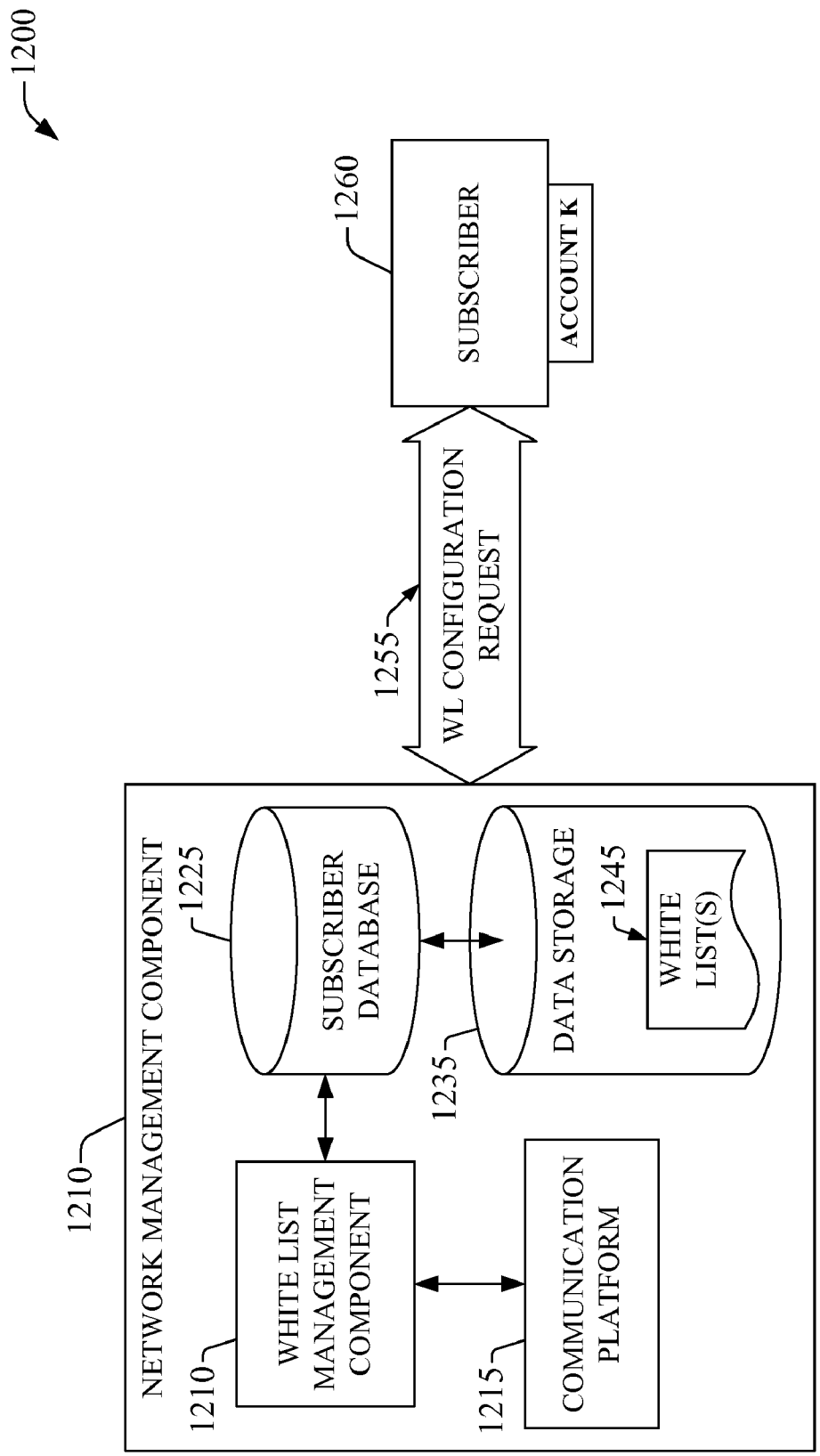
FIG. 12 illustrates a block diagram of an example system that can facilitate addition of subscriber(s)/subscriber station(s) to one or more white lists associated with a femtocell in accordance with an aspect of the disclosed subject matter.

FIG. 12 is a block diagram of an example system 1200 that can facilitate addition of subscriber(s)/subscriber station(s) to one or more white lists associated with a femtocell (e.g., femto AP 130) in accordance with an aspect of the disclosed subject matter. In example system 1200, a network management component 1210 can include a white list management component 1210 which can be coupled to a subscriber database 1225, a data storage 1235, and a communication platform 1215. The white list management component 1210 can data-mine subscriber database 1225 and white list(s) 1245, which can reside in data storage 1235, to drive addition of new subscribers to a white list to request reciprocal adding. In an aspect, once a subscriber 1260 in account K is identified for reciprocal addition at a time the subscriber 1260 configures his/her femto AP (e.g., 130), a white list (WL) configuration request 1255 can be conveyed (e.g., via a wired or wireless link through communication platform 1215) to the subscriber. Such configuration request can indicate that a disparate subscriber has subscriber 1260 white-listed and can prompt subscriber 1260 to include in his/her white list the disparate subscriber.

An illustrative scenario is the following: User 1 adds User 2 to his/her white list. Once User 2 configures/activates his/her femtocell, a setup process (e.g., implemented through a web-based online GUI) can prompt User 2 to add User 1. It is to be noted that the white list management component 1210 can exploit information in subscriber database 1225 and data storage 1235 to inform User 2 of substantially all subscriber station numbers, codes or tokens that he/she can automatically add to his/her white list on a reciprocity basis; namely, User 2 can be prompted to add in the white list(s) of User 2 those subscribers that have previously added him/her to their white list(s). In an aspect, the white list configuration request 1255 can be effected through one or more of various interfaces, such as an online GUI; a real time prompt/alert delivered via SMS, MMS, email, instant message; etc.

Figure 13:
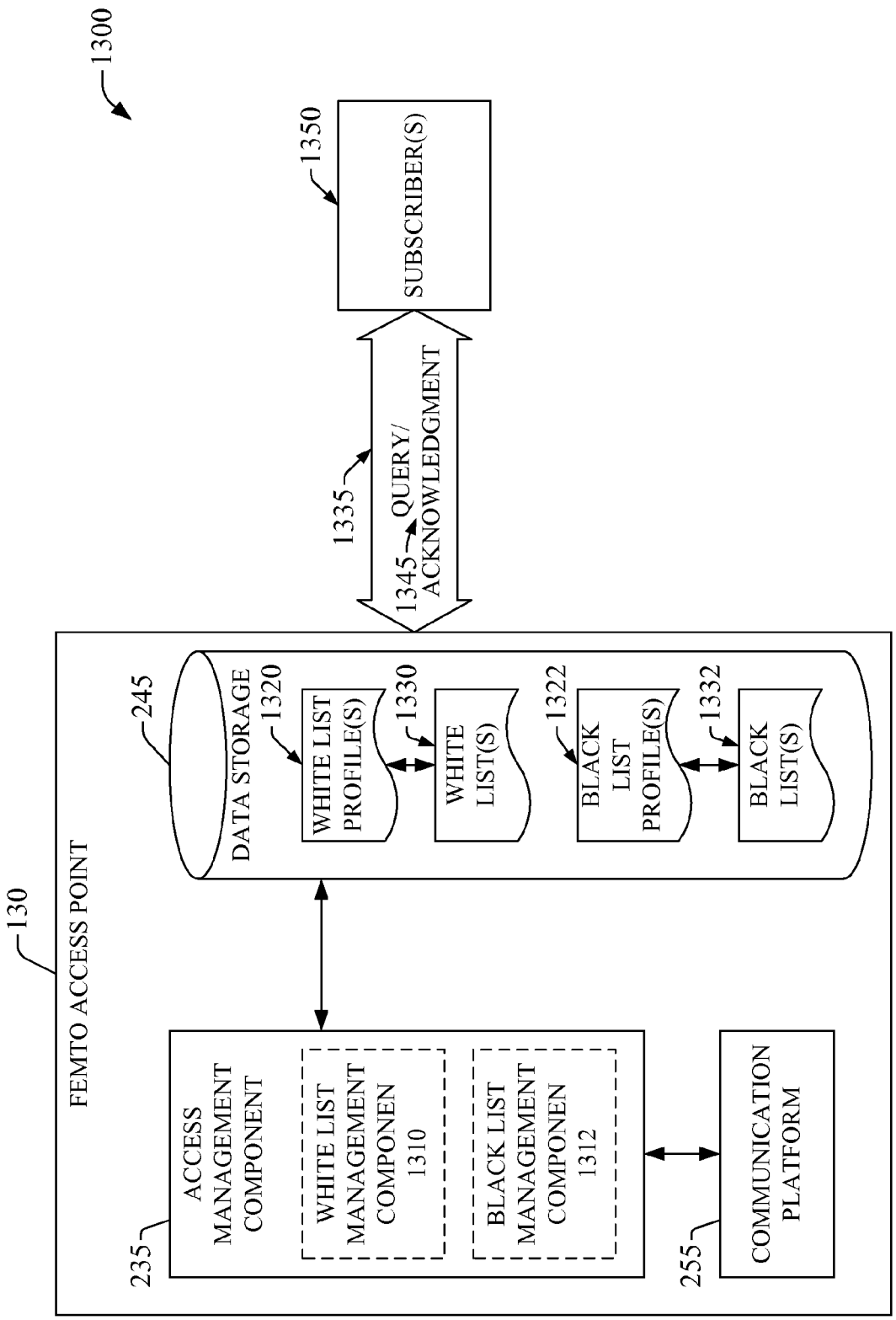
FIG. 13 depicts a block diagram of an example system that can manage a defined logic relating to maintaining content(s) in a white list(s) on a white list database and a black list(s) in a black list database in accordance with an aspect of the disclosed subject matter.

FIG. 13 is a block diagram of an example system 1300 that can manage a defined logic relating to maintaining content(s) (e.g., MSISDNs) in a white list(s) (e.g., access control list(s)) on a white list database and a black list(s) in a black list database in accordance with an aspect of the disclosed subject matter. In an aspect, the access management component 235, which can comprise a white list management component 1310, can develop a white list profile(s) 1320 that can apply logic and parameters that can facilitate controlling, or managing, content, such as subscriber station numbers (e.g., MSISDNs), codes or tokens, in a white list(s) 1330. White list profile(s) 1320 and white list(s) 1330 can be stored in data storage 245; it should be appreciated that while data storage 245 is illustrated to reside within femto AP 130, such storage can reside in a network management component (e.g., component 1210).

In another aspect, white list profile parameters that can facilitate controlling utilization logic of white list(s) content can include, without being limited to including: (i) temporary access, e.g., full access for a specific time interval, such as a specified number of days, hours, or minutes; (ii) access only within a window of time in a day (e.g., voice and data allowed from 9:00 a.m.-6:00 p.m., or voice allowed after 9:00 p.m.) which can facilitate billing schemes already established by an operator/service provider); and/or (iii) access to specific applications, such as scheduler, calendar(s), news streaming, authoring tools, gaming, video and music, etc.

In still another aspect, logic within white list profile(s) can implement parameters to determine how long access to femto coverage is granted. For instance, when a timer associated with temporary access of a subscriber station (e.g., communication device) expires, a query 1345 can be conveyed (e.g., through a wired or wireless link 1335) to either a subscriber that operates a device associated with the managed MSISDN in order to request renewed access, or to a subscriber that operates femto AP 130. The message request, e.g., query 1345, can ask the owner if an extension of time is to be granted or not. When a request is not granted by a subscriber that operates femto AP 130 or there is no reply, e.g., acknowledgement 1345, from the subscriber, access to femto coverage can expire and information, such as the MSISDN (or substantially any identifier code or token), associated with the subscriber station can be deleted from a corresponding white list(s) within data storage 245. Conversely, a positive response, e.g., acknowledgement 1345, can allow access to continue for the subscriber station based at least in part on parameters extant in white list profile(s) or newly defined parameters. It is to be noted that query 1345 can be conveyed via an online GUI, an email message, a SMS message, MMS message, a voice mail, a web prompt, and the like.

In yet another aspect, the access management component 235 can comprise a black list management component 1312 and can develop a black list profile(s) 1322 that can apply logic and parameters that can facilitate controlling, or managing, content, such as subscriber station numbers (e.g., MSISDNs), codes or tokens, in a black list(s) 1332. The black list profile(s) 1322 and black list(s) 1332 can be stored in data storage 245.

In an aspect, black list profile parameters that can facilitate controlling utilization logic of block list(s) content can include, without being limited to including: temporary denial of access of the femto AP by the subscriber station until a black-list condition(s) is met, where the black-list condition(s) can comprise information related to the subscriber station (e.g., 310) temporarily remains on the black list(s) 1332 for a predetermined amount of time, information related to the subscriber station temporarily remains on the black list(s) 1332 until the subscriber station 310 leaves the coverage area of the femto AP, and/or information related to the subscriber station temporarily remains on the black list(s) 1332 until the subscriber station is powered down (e.g., turned off, battery discharged, . . . ) or re-booted; and/or permanent (or semi-permanent) denial of access of the femto AP by the subscriber station. When a black-list condition(s) is met, denial of access to femto coverage can expire and information, such as the MSISDN (or substantially any identifier code or token), associated with the subscriber station can be deleted from a corresponding black list(s) within data storage 245.

Figure 14:
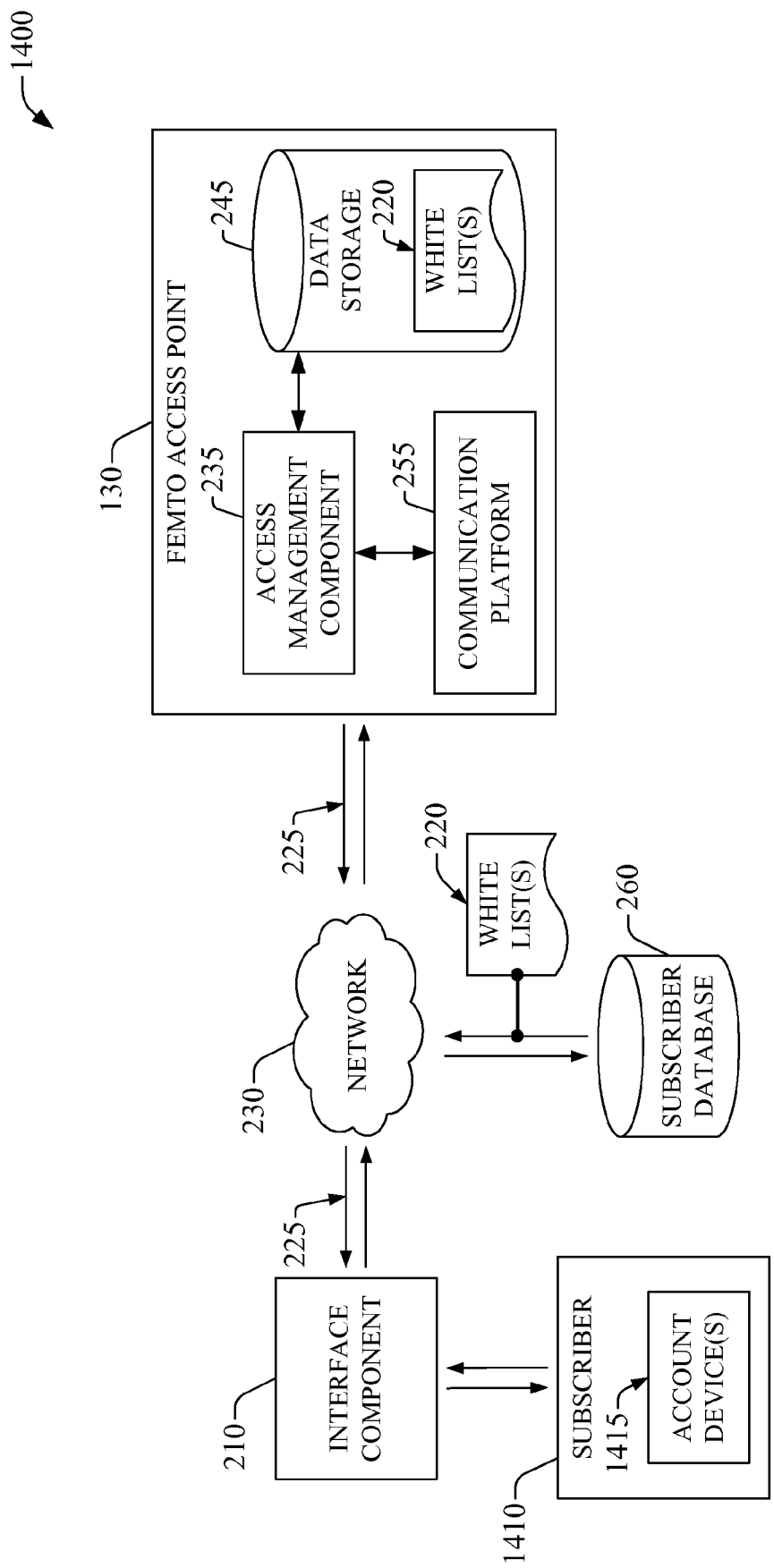
FIG. 14 illustrates a block diagram of an example system that can initialize a white list(s) to femto coverage for a subscriber station with available subscriber station identifier numbers, codes or tokens available on a service account in accordance with an aspect of the disclosed subject matter.

FIG. 14 is a block diagram of an example system 1400 that can initialize a white list(s) (e.g., access control list(s)) to femto coverage for a subscriber station with available subscriber station identifier numbers, codes or tokens available on a service account in accordance with an aspect of the disclosed subject matter. In example system 1400, a subscriber 1410 who can utilize account device(s) 1415, can provision femto AP 130 and associate the account device(s) 1415 with a service account via a networked interface component 210 (e.g., an online account management system) which can look up into substantially all subscriber station(s) identifier numbers (e.g., MSISDNs), codes or tokens associated with the service account, and can automatically populate white list(s) 220 with the extracted subscriber station(s) numbers, codes or tokens. Subscriber 1410, via interface component 210, can remove or add subscriber station(s) numbers (e.g., MSISDNs), codes or tokens extant in a pre-populated white list(s) 220; additional edits can be performed as well, based at least in part on the complexity of white list(s) 220. In an aspect, to pre-set white list(s) 220, the networked interface component 210 can access information stored in subscriber database 260 through network 230, which can include information technology systems of a service provider. White list(s) 220 can be conveyed through network 230 to femto AP 130; a communication platform 255 can receive white list(s) 220 and access management component 235 can store the white list(s) 220 in data storage 245.

Illustrative advantages provided by example system 1400 can include (a) reduced femtocell provisioning lead time, and (b) immediate utilization of a femtocell with mobile numbers that belong to a same service account, whether subscribers of such numbers subscribe to the femtocell or a feature application, or code, that delivers a femtocell service.

Figure 15:
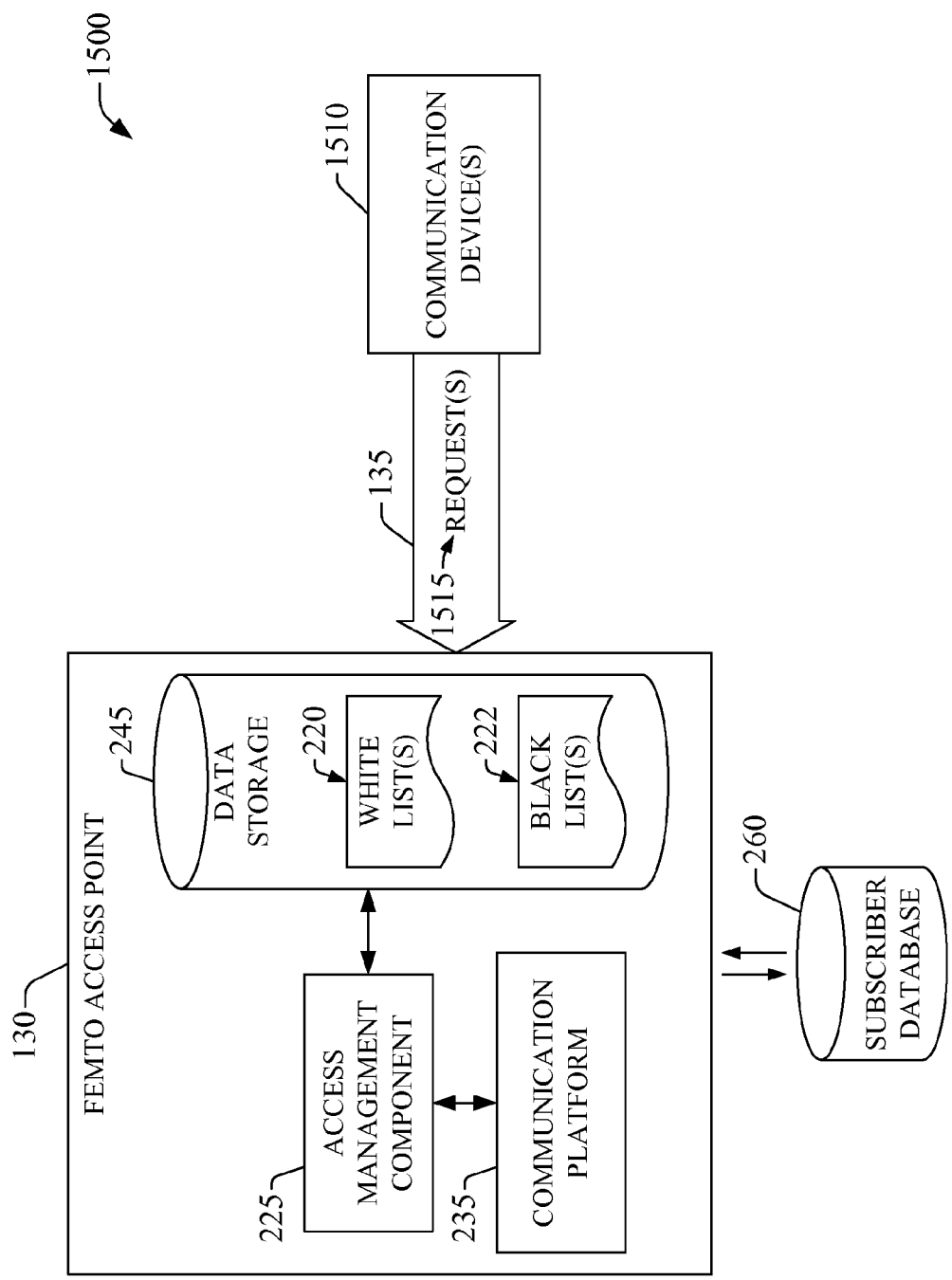
FIG. 15 depicts a block diagram of an example system that can facilitate management of access of a femto access point by a communication device on a request from the communication device in accordance with an aspect of the disclosed subject matter.

FIG. 15 is a block diagram of an example system 1500 that can facilitate management of access of a femto AP by a communication device on a request(s) from the communication device in accordance with an aspect of the disclosed subject matter. For instance, in example system 1500, the communication device 1510 can transmit a request to the femto AP 130 to facilitate being placed on a white list(s) 220 associated with the femto AP 130 and accessing the femto AP 130 and associated services or content, or can transmit a request to the femto AP 130 to facilitate updating information (e.g., identifier number of the communication device) associated with the communication device 1510 in the white list(s) 220. In example system 1500, communication device(s) 1510 (e.g., subscriber station(s), such as a mobile phone) can convey a request(s) or query(ies) 1515 to facilitate accessing coverage of femto AP 130. The query 1515 can be conveyed via an online GUI, an email message, a SMS message, MMS message, a voice mail, a web prompt, USSD (or * and # codes), and the like. Such request 1515 can be received by communication platform 255, and access management component 235 can be configured to allow or reject the request; allowance or rejection of a request can be based at least in part on various metrics, such as security, type of communication device, profile of subscriber that operates/operated the communication device 1510 that requests access, etc. Upon allowance of a request, the access management component 235 can query for available slots to be filled in white list(s) 220 associated with accounts served by femto AP 130, and when space is available for a subscriber station identifier number (e.g., MSISDN), code or token, the query can further probe whether access is allowed on a permanent or temporary basis (e.g., to reduce risk exposure to security problems, maintain available space on white list(s) 220 for other communication devices 1510, etc.). Characteristics of femto coverage allowance can be set or pre-set through the access management component 235. Subsequent to allowance and examination of information related to relevant white list(s) 220, access management component 235 can update white list(s) 220, stored in data storage 245, to reflect the approved request for femto coverage by the femto AP 130. It is to be noted that access and update of collected subscriber identifier numbers (e.g., MSISDN), codes or token, can also be effected through network-based white list database(s). Information (e.g., wireless device numbers, codes or tokens (e.g., MSISDNs); subscriber's active numbers, codes or tokens; and numbers, codes or tokens on service accounts in good standing, . . . ) related to communication devices 310 can be provided through networked access to a subscriber database 260.

An illustrative, non-limiting advantage of example system 1500 is that it can provide an enhanced end user experience with a direct, clear mechanism and thus can encourage use of the femto AP 130, and can avoid time spent on edition of white list(s) through a networked interface (e.g., interface component 210) like an online interface which can take time for the end user to have access to the Internet, and to log on in a secured interface.

In another aspect, if the request 1515 is rejected by the access management component 235, or if there is no available slot in the white list(s) 220 and associated femto AP 130, the access management component 235 can deny access of the femto AP 130 to the communication device 1510. The communication device 1510 also can be placed on a black list(s) 222 associated with the femto AP 130, and stored in data storage 245, on a permanent (or semi-permanent) or temporary basis, for example, by the access management component 235. For instance, if the access management component 235 determines that the communication device 1510 is not to be granted access to coverage by the femto AP 130 on a permanent basis based at least in part on predefined access criteria, the access management component 235 can facilitate updating the black list(s) 222, and storing the black list(s) 222 in data storage 245, to include information related to the communication device 1510, where the communication device 1510 can be listed in the black list(s) 222 on a permanent (or semi-permanent) basis.

In yet another aspect, if access to the femto AP 130 is denied by the access management component 235 at this time (e.g., due to no available slot on the white list(s)), the black list(s) 222 can be updated to include information related to the communication device 1510 on the black list(s) 222 on a temporary basis, for example, by the access management component 235, where the black list(s) 222 can be stored in data storage 245. The communication device 1510 can remain on the black list(s) 222 until a predefined black-list condition(s) is met. The predefined black-list conditions can comprise, for example, the communication device 1510 temporarily remains on the black list(s) 222 for a predetermined amount of time, the communication device 1510 temporarily remains on the black list(s) 222 until the communication device 1510 leaves the coverage area of the femto AP 130, and/or the communication device 1510 temporarily remains on the black list(s) 222 until the communication device 1510 is powered down (e.g., turned off, battery discharged, . . . ) or re-booted, as desired. Once a black-list condition is met, the access management component 235 can facilitate updating the black list(s) 222 to delete information related to the communication device 1510 from the black list(s) 222, and the updated black list(s) 222 can be stored in data storage 245.

While on the black list(s) 222 (temporarily or permanently (or semi-permanently)), the communication device 1510 is not eligible for access to or to attempt access to the femto AP 130. Employing black list(s) 222 can facilitate reducing signaling (e.g., unnecessary signaling) between communication devices and the femto AP 130, as it will be unnecessary for signaling by the femto AP 130 to a black-listed communication device with regard to the black-listed communication device accessing the femto AP 130; can facilitate reduced power consumption by the femto AP 130 and/or the black-listed communication device due in part to the reduced signaling; and can facilitate more efficient communication between the femto AP 130 and communication devices 310 in the coverage area of the femto AP 130, since unnecessary signaling can be reduced.

It is to be appreciated that substantially any wireless communication device 1510 within coverage area of femto AP 130 (e.g., area 125) can request access without intervention by a subscriber that operates femto AP 130, and who has previously entered a set of subscriber station numbers (e.g., MSISDNs), codes or tokens, via a networked interface (e.g., interface component 210). Once a request is granted, a secure tunnel can be established from the device/client through the femtocell's IP connection or the default of the Radio Access Network if the IP connection is not available. Secure layers including utilizing the femtocell's VPN and/or USSD would ensure that the transaction is in fact secure.

In accordance with still another aspect of the subject innovation, the example system 1500 can track subscriber station identifier numbers (e.g., MSISDNs, IMSIs), codes or tokens, associated with white list(s) on record with a femto service provider. When a subscriber (e.g., subscriber A 1010), or end user, that operates communication device(s) 1510 cancels an account or subscription with a service provider or changes an identifier number, a code, or a token associated with communication device(s) 1510, the subscriber can convey a request 1515 via communication device(s) 1510 to remove the identifier number thereof from substantially all, or all, white list(s) 220 on record in a subscriber database 260 or substantially any other database available to a service provider that contains information on service subscribers. In an aspect, the access management component 235 can convey an indication, via backhaul pipe 140, to update white lists to a mobile wireless platform (e.g., a core network) in accordance to request(s) 1515. It is noted that local records of white list(s) 220 also can be updated; local update can take place in all femto APs that include white list(s) 220 that comprise the identifier number communication device 1510 that is updated.

Additionally, or alternatively, when an end user changes their mobile or subscriber station number, code or token, (e.g., after relocation to a new area code, or the like), the communication device 1510 can convey a request(s) 1515 to femto AP 130 to automatically update substantially all, or all, white list(s) 220 on record that include the identifier number, code, or token of the communication device 1510. Access management component 235 can deliver signaling via backhaul pipe 140 to a mobile network platform to update white list(s) 220 records in subscriber database 260. It is noted that local records of white list(s) 220 also can be updated.

An illustrative advantage of such on-request automatic update of white list(s) in the subscriber database 260, and local white list(s) 220, is ease of use for end users to maintain current white lists at the network level and local, e.g., femto AP 130, level without a need to track each subscriber station number, code, or token associated with the white list(s) stored in the subscriber database 260. In addition, updated white list(s) in the subscriber database 260 and local white list(s) 220 can maintain the value proposition of the femtocells for end users and service operator by a seamless move of traffic off of the macro network (e.g., a WAN) to femto network(s).

Figure 16:
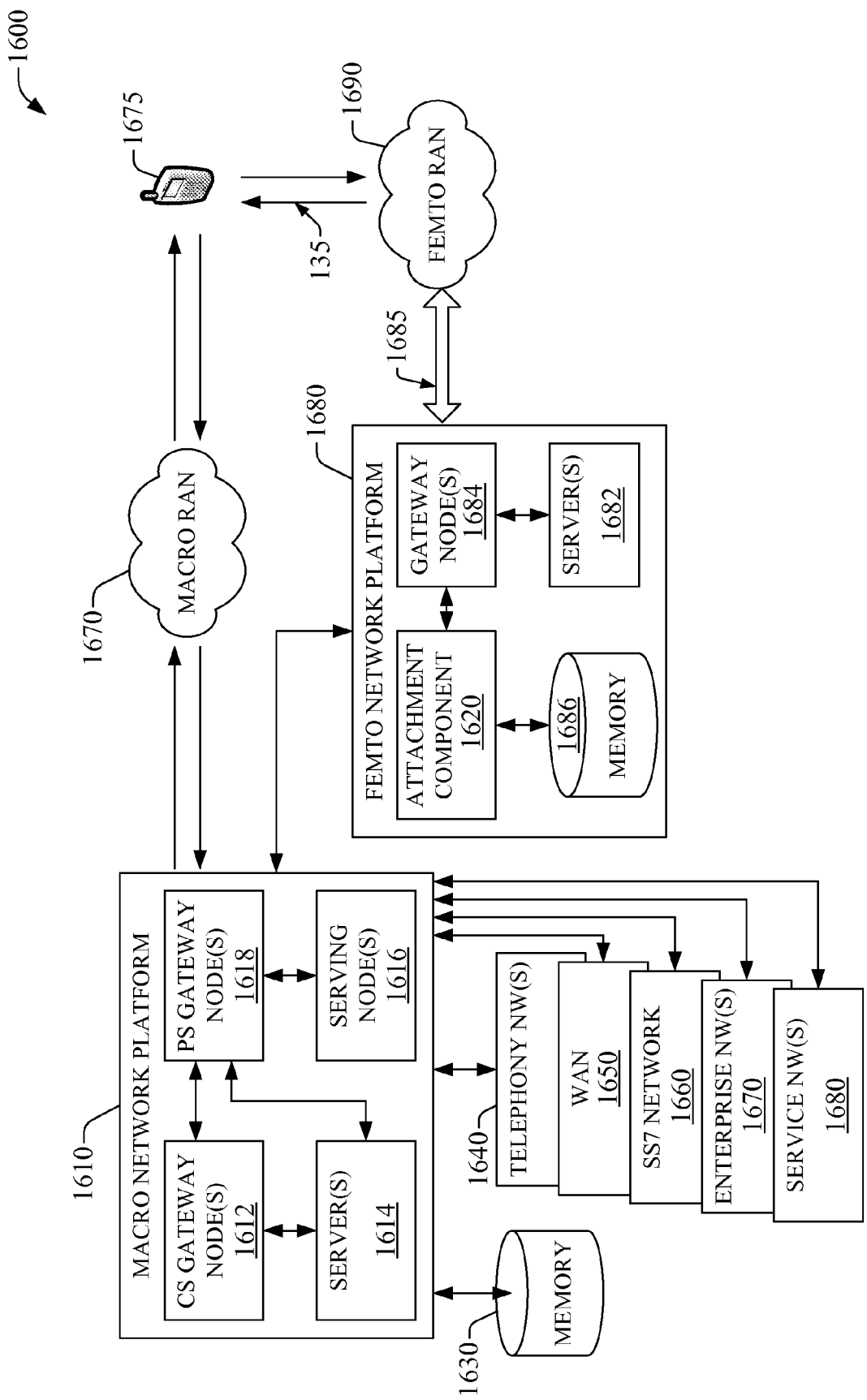
FIG. 16 depicts a block diagram of example macro and femto wireless network environments that can exploit femto APs in accordance with various aspects of the disclosed subject matter.
Figure 17:
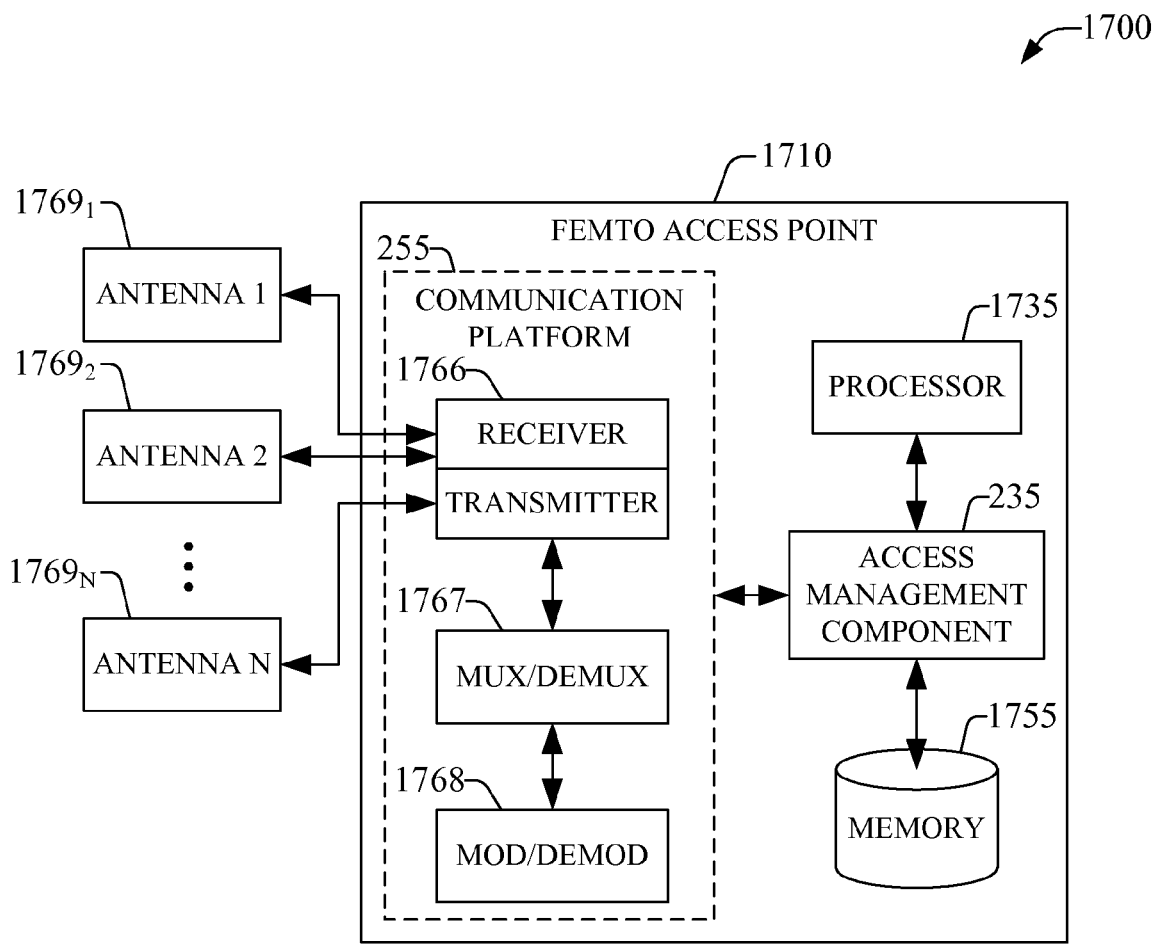
FIG. 17 is a block diagram of an example femto access point that operates in accordance with aspects disclosed in the subject specification.

To provide further context for various aspects of the subject specification, FIG. 16 and FIG. 17 illustrate, respectively, example macro and femto wireless network environments that can exploit femto APs and a block diagram of an example embodiment of a femtocell access point that can enable and exploit features or aspects of the subject innovation and that utilize aspects of the subject innovation in accordance with various aspects of the subject specification.

With respect to FIG. 16, wireless communication environment 1600 includes two wireless network platforms: (i) A macro network platform 1610 which serves, or facilitates communication with user equipment 1675 (e.g., mobile $120_A$) via a macro radio access network (RAN) 1670. It should be appreciated that in cellular wireless technologies (e.g., 3GPP UMTS, HSPA, 3GPP LTE, 3GPP2 UMB), macro network platform 1610 is embodied in a Core Network. (ii) A femto network platform 1680, which can provide communication with ULE 1675 through a femto RAN 1690, which is linked to the femto network platform 1680 via backhaul pipe(s) 1685 (e.g., backhaul link(s) 153). It should be appreciated that macro network platform 1610 typically hands off UE 1675 to femto network platform 1610 once UE 1675 attaches (e.g., through macro-to-femto handover) to femto RAN 1690, which includes a set of deployed femto APs (e.g., femto AP 130) that can operate in accordance with aspects described herein.

It is noted that RAN includes base station(s), or access point(s), and its associated electronic circuitry and deployment site(s), in addition to a wireless radio link operated in accordance with the base station(s). Accordingly, macro RAN 1670 can comprise various coverage cells like cell 105, while femto RAN 1690 can comprise multiple femtocell access points such as femto AP 130. Deployment density in femto RAN 1690 can be substantially higher than in macro RAN 1670.

Generally, both macro and femto network platforms 1610 and 1680 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject innovation, macro network platform 1610 includes CS gateway node(s) 1612 which can interface CS traffic received from legacy networks like telephony network(s) 1040 (e.g., public switched telephone network (PSTN), or public land mobile network (PLMN)) or a SS7 network 1660. Circuit switched gateway 1612 can authorize and authenticate traffic (e.g., voice) arising from such networks. Additionally, CS gateway 1612 can access mobility, or roaming, data generated through SS7 network 1660; for instance, mobility data stored in a VLR, which can reside in memory 1630. Moreover, CS gateway node(s) 1612 interfaces CS-based traffic and signaling and gateway node(s) 1618. As an example, in a 3GPP UMTS network, PS gateway node(s) 1618 can be embodied in gateway GPRS support node(s) (GGSN).

In addition to receiving and processing CS-switched traffic and signaling, PS gateway node(s) 1618 can authorize and authenticate PS-based data sessions with served (e.g., through macro RAN) wireless devices. Data sessions can include traffic exchange with networks external to the macro network platform 1610, like wide area network(s) (WANs) 1650, enterprise networks (NW(s)) 1670 (e.g., enhanced 911), or service NW(s) 1680 like IP multimedia subsystem (IMS); it should be appreciated that local area network(s) (LANs), which may be a part of enterprise NW(s), can also be interfaced with macro network platform 1610 through PS gateway node(s) 1618. Packet-switched gateway node(s) 1618 generates packet data contexts when a data session is established. To that end, in an aspect, PS gateway node(s) 1618 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 1614. It is to be noted that in 3GPP UMTS network(s), gateway node(s) 1018 (e.g., GGSN) and tunnel interface (e.g., TTG) comprise a packet data gateway (PDG).

Macro network platform 1610 also includes serving node(s) 1616 that convey the various packetized flows of information, or data streams, received through PS gateway node(s) 1618. As an example, in a 3GPP UMTS network, serving node(s) can be embodied in serving GPRS support node(s) (SGSN).

As indicated above, server(s) 1614 in macro network platform 1610 can execute numerous applications (e.g., location services, online gaming, wireless banking, wireless device management, . . . ) that generate multiple disparate packetized data streams or flows, and manage (e.g., schedule, queue, format . . . ) such flows. Such application(s), for example can include add-on features to standard services provided by macro network platform 1610. Data streams can be conveyed to PS gateway node(s) 1618 for authorization/authentication and initiation of a data session, and to serving node(s) 1616 for communication thereafter. Server(s) 1614 can also effect security (e.g., implement one or more firewalls) of macro network platform 1610 to ensure network's operation and data integrity in addition to authorization and authentication procedures that CS gateway node(s) 1612 and PS gateway node(s) 1618 can enact. Moreover, server(s) 1614 can provision services from external network(s), e.g., WAN 1650, or Global Positioning System (GPS) network(s), which can be a part of enterprise NW(s) 1680. It is to be noted that server(s) 1614 can include one or more processor configured to confer at least in part the functionality of macro network platform 1610. To that end, the one or more processor can execute code instructions stored in memory 1630, for example.

In example wireless environment 1600, memory 1630 stores information related to operation of macro network platform 1610. Information can include business data associated with subscribers; market plans and strategies, e.g., promotional campaigns, business partnerships; operational data for mobile devices served through macro network platform; service and privacy policies; end-user service logs for law enforcement; and so forth. Memory 1630 can also store information from at least one of telephony network(s) 1640, WAN 1650, SS7 network 1660, enterprise NW(s) 1670, or service NW(s) 1680.

Regarding femto network platform 1680, it includes a femto gateway node(s) 1684, which have substantially the same functionality as PS gateway node(s) 1618. Additionally, femto gateway node(s) 1684 can also include substantially all functionality of serving node(s) 1616. Disparate gateway node(s) 1684 can control or operate disparate sets of deployed femto APs, which can be a part of femto RAN 1690. In an aspect of the subject innovation, femto gateway node(s) 1684 can aggregate operational data received from deployed femto APs. Moreover, femto gateway node(s) 1684, can convey received attachment signaling to attachment component 1620. It should be appreciated that while attachment component is illustrated as external to gateway node(s) 1684, attachment component 1620 can be an integral part of gateway node(s) 1684.

Attachment component 1620 can facilitate macro-to-femto and femto-to-macro handover with attachment to a femto AP (e.g., femto AP 130) dictated in accordance to a white list (e.g., white list(s) 220) and/or a white list profile (e.g., white list profile(s) 1320). In an aspect, attachment component 1620 can include a determination of whether a white list resides within femto AP and whether a mobile station that is attempting attachment is whitelisted as described in the subject innovation. It is noted, in an aspect, that when a whitelisted mobile station is allowed to attach to the femto AP, attachment component 1620 can establish femto service in accordance with privileges, or access logic, configured in a white list profile (e.g., white list profile(s) 220).

Memory 1686 can retain additional information relevant to operation of the various components of femto network platform 1680. For example operational information that can be stored in memory 1686 can comprise, but is not limited to, subscriber intelligence; contracted services; maintenance and service records; femto cell configuration (e.g., devices served through femto RAN 1690; authorized subscribers associated with one or more deployed femto APs); service policies and specifications; privacy policies; add-on features; so forth.

Server(s) 1682 have substantially the same functionality as described in connection with server(s) 1614. In an aspect, server(s) 1682 can execute multiple application(s) that provide service (e.g., voice and data) to wireless devices served through femto RAN 1690. Server(s) 1682 can also provide security features to femto network platform. In addition, server(s) 1682 can manage (e.g., schedule, queue, format . . . ) substantially all packetized flows (e.g., IP-based, frame relay-based, ATM-based) it generates in addition to data received from macro network platform 1610. Furthermore, server(s) 1682 can effect provisioning of femto cell service, and effect operations and maintenance. It is to be noted that server(s) 1682 can embody a provisioning server, and can populate white list(s) and white list profile(s) in accordance with aspects described herein. It is to be noted that server(s) 1682 can include one or more processors configured to provide at least in part the functionality of femto network platform 1680. To that end, the one or more processors can execute code instructions stored in memory 1686, for example.

With respect to FIG. 17, in embodiment 1700, femto AP 1710 can receive and transmit signal(s) from and to wireless devices like macro and femto access points, access terminals, wireless ports and routers, and the like, through a set of antennas $1769_1$-$1769_N$. It should be appreciated that while antennas $1769_1$-$1769_N$ are a part of communication platform 255, which comprises electronic components and associated circuitry that provides for processing and manipulation of received signal(s) and signal(s) to be transmitted. In an aspect, communication platform 255 includes a receiver/transmitter 1766 that can convert signal from analog to digital upon reception, and from digital to analog upon transmission. In addition, receiver/transmitter 1766 can divide a single data stream into multiple, parallel data streams, or perform the reciprocal operation. Coupled to receiver/transmitter 1766 is a multiplexer/demultiplexer 1767 that facilitates manipulation of signal in time and frequency space. Electronic component 1767 can multiplex information (e.g., data/traffic and control/signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 1767 can scramble and spread information (e.g., codes) according to substantially any code known in the art; e.g., Hadamard-Walsh codes, Baker codes, Kasami codes, polyphase codes, and so on. A modulator/demodulator 1768 is also a part of operational group 1725, and can modulate information according to multiple modulation techniques, such as frequency modulation, amplitude modulation (e.g., M-ary quadrature amplitude modulation (QAM), with M a positive integer), phase-shift keying (PSK), and the like.

Femto access point 1710 also includes a processor 1735 configured to confer functionality, at least partially, to substantially any electronic component in the femto access point 1710. In particular, processor 1735 can facilitate access management component 235 supplying fixed differentiated QoS in accordance with aspects disclosed herein. In addition, processor 1735 can facilitate operations on data (e.g., symbols, bits, or chips) for multiplexing/demultiplexing, such as effecting direct and inverse fast Fourier transforms, selection of modulation rates, selection of data packet formats, inter-packet times, etc. A memory 1755 can store data structures, code instructions, system or device information like policies and specifications, code sequences for scrambling, spreading and pilot transmission, floor plan configuration, access point deployment and frequency plans, scheduling policies, and so on.

In embodiment 1700, processor 1734 is coupled to the memory 1755 in order to store and retrieve information necessary to operate and/or confer functionality to communication platform 255, access management component 235, and other operational aspects of femto access point 1710.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," data storage," "database," and substantially any other information storage component relevant to operation and functionality of a component, refer to "memory components," or entities embodied in a "memory" or components comprising the memory. For example, information relevant to operation of various components described in the disclosed subject matter, and that can be stored in a memory, can comprise, but is not limited to comprising, subscriber information; femtocell configuration (e.g., devices served by a femto AP; access control lists, or white lists) or service policies and specifications; privacy policies; and so forth. It will be appreciated that the memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), phase change memory (PCM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Various aspects or features described herein may be implemented as a method, apparatus, or article of manufacture using standard programming and/or engineering techniques. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD), Blu-ray disc (BD), . . . ), smart cards, and flash memory devices (e.g., card, stick, key drive . . . ).

What has been described above includes examples of systems and methods that provide advantages of the subject innovation. It is, of course, not possible to describe every conceivable combination of components or methodologies for purposes of describing the claimed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:
1. A system, comprising:
an access management component that scans a frequency band and detects at least one communication device in response to a determination that the at least one communication device has entered a femtocell coverage area associated with a femtocell, automatically generates and transmits a query to the at least one communication device in response to detection of the at least one communication device in the femtocell coverage area of the femtocell to prompt the at least one communication device to request access to the femtocell and be entered on a data storage associated with the femtocell, and grants access to the femtocell and a subset of services associated with the femtocell to the at least one communication device, based on the data storage and at least one predefined access criterion; and
the femtocell that facilitates provision of access of the femtocell and the subset of services to the at least one communication device.

2. The system of claim 1, wherein the access management component detects resources available in the at least one communication device and functions supported by the at least one communication device.

3. The system of claim 2, wherein the access management component automatically generates and transmits a query to the at least one communication device to prompt the at least one communication device to indicate type of access of the femtocell requested by the at least one communication device.

4. The system of claim 3, wherein the access management component determines whether the type of access of the femtocell requested by the at least one communication device is available.

5. The system of claim 4, wherein the access management component grants access of the femtocell and the subset of services based on the type of access of the femtocell requested by the at least one communication device when available, and, in response to the type of access of the femtocell not being available, prompts the at least one communication device to request another type of access of the femtocell.

6. The system of claim 1, wherein the access management component monitors activity associated with access to the femtocell and the subset of services by the at least one communication device.

7. The system of claim 6, wherein the access management component determines whether the at least one communication device has been inactive in relation to accessing the femtocell and the subset of services for at least a predefined period of time.

8. The system of claim 7, wherein the access management component automatically generates and transmits a query to the at least one communication device to prompt the at least one communication device to indicate whether the at least one communication device requests to continue access to the femtocell and the subset of services.

9. The system of claim 8, wherein the access management component continues to grant access to the femtocell and the subset of services to the at least one communication device in response to receipt of a request for continued access by the access management component, and, in response to no request for continued access being received, terminates access to the femtocell and the subset of services.

10. The system of claim 1, wherein the subset of services comprises access to content.

11. The system of claim 1, further comprising:
a content provider that is connected to the femtocell and provides content to the at least one communication device via the femtocell; and
a service provider that is connected to the femtocell and provides a service to the at least one communication device via the femtocell.

12. The system of claim 11, wherein the at least one service provider employs a communication device with computational capabilities to facilitate provision of the service.

13. The system of claim 1, wherein the femtocell facilitates provision of information, which relates to the subset of services, to the at least one communication device at a broadband data transmission rate that is a faster rate than a data transmission rate associated with over-the-air data transmission via a macro base station.

14. The system of claim 1, wherein the access management component transmits a permanency query to the at least one communication device, wherein the permanency query prompts the at least one communication device to indicate whether the at least one communication device requests to be added to the data storage on a permanent basis.

15. The system of claim 1, wherein the access management component stores information relating to the at least one communication device in the data storage.

16. The system of claim 15, wherein the information comprises information that identifies the at least one communication device, bandwidth-related information associated with the at least one communication device, and historical data relating to use of the femtocell by the at least one communication device.

17. The system of claim 1, wherein predefined access criteria, comprising the at least one predefined access criterion, relates to functions supported by the at least one communication device, type of access requested by the at least one communication device, and historical data associated with the at least one communication device in relation to the femtocell.

18. The system of claim 1, wherein the access management component denies access to the femtocell and the subset of services to at least one other communication device based on the at least one predefined access criterion and enters information relating to the at least one other communication device on a black list associated with the femtocell.

19. A method, comprising:
scanning a frequency spectrum associated with wireless communications to facilitate detecting a mobile communication device in a cell coverage area of a femto access point;
detecting the mobile communication device when the mobile communication device is located within the cell coverage area;
automatically prompting the mobile communication device detected in the cell coverage area to request to access the femto access point and a subset of services provided via the femto access point and to be entered on an access control list;
updating the access control list to include information relating to the mobile communication device; and
granting access of the femto access point and the subset of services to the mobile communication device based on information in the access control list, level of access granted to the mobile communication device, and at least one predefined access criterion.

20. The method of claim 19, further comprising:
automatically generating a query to prompt the mobile communication device to request to be entered on the access control list and access the femto access point and the subset of services, in response to the detecting of the mobile communication device; and
transmitting the query to the mobile communication device.

21. The method of claim 19, further comprising:
detecting information relating to a subset of functions supported by the mobile communication device;
prompting the mobile communication device to have the mobile communication device indicate type of access requested by the mobile communication device;
receiving information that indicates the type of access requested by the mobile communication device; and
determining access of the femto access point and the subset of services that is to be granted to the mobile communication device based on the detected information and the received information.

22. The method of claim 19, further comprising:
storing the detected information and the received information in the access control list.

23. The method of claim 19, further comprising:
monitoring the access of the femto access point and the subset of services by the mobile communication device; and
determining whether the mobile communication device has been inactive with regard to accessing the femto access point and the subset of services for at least a predefined period of time.

24. The method of claim 23, further comprising:
prompting the mobile communication device to indicate whether the mobile communication device requests to continue access of the femto access point and the subset of services when the mobile communication device is determined to have been inactive with regard to accessing the femto access point and the subset of services for at least the predefined period of time.

25. The method of claim 24, further comprising:
controlling whether to continue access to the femto access point and the subset of services by the mobile communication device based on response of the mobile communication device to the prompting of the mobile communication device to indicate whether the mobile communication device requests to continue access of the femto access point and the subset of services.

26. The method of claim 19, further comprising:
inferring, based on current information and historical information relating to the mobile communication device, a level of access to be granted to a mobile communication device with regard to the femto access point.

27. The method of claim 26, further comprising:
collecting historical information associated with the mobile communication device;
storing the historical information;
analyzing the historical information and the current information associated with the mobile communication device, to facilitate generating at least one inference relating to the level of access to the femto access point that is to be granted to the mobile communication device.

28. The method of claim 19, further comprising:
connecting at least one service provider to the femto access point; and
controlling access, by the mobile communication device, to the subset of services associated with the at least one service provider based on the access control list.

29. The method of claim 19, wherein predefined access criteria, comprising the at least one predefined access criterion, relates to slot availability associated with the femto access point, and current and historical data associated with the mobile communication device.

30. The method of claim 19, further comprising:
denying access of the femto access point and the subset of services to at least one other mobile communication device based on the at least one predefined access criterion; and
storing information related to the at least one other mobile communication device in a black list(s) associated with the femto access point.

31. The method of claim 19, further comprising:
transmitting information relating to the subset of services to the mobile communication device at a broadband data transmission rate.

32. The method of claim 19, the subset of services comprising a voice service and a service that provides access to content.

33. The method of claim 19, further comprising:
receiving a request to update a subset of the information associated with the mobile communication device stored in the access control list;
updating the subset of the information associated with the mobile communication device stored in the access control list based on the received request; and
storing the updated access control list.

34. The method of claim 33, the subset of the information comprising information that identifies an identifier number associated with the mobile communication device.

35. A non-transitory computer-readable medium having instructions stored thereon that, in response to execution, cause a computing device including a process to perform acts, comprising:
scanning a frequency spectrum associated with wireless communications to facilitate detecting at least one subscriber station in a femtocell coverage area of a femtocell;
detecting the at least one subscriber station when the at least one subscriber station is located within the femtocell coverage area;
automatically querying the at least one subscriber station detected in the femtocell coverage area of the femtocell to prompt the at least one subscriber station to request to be entered on an access control list associated with the femtocell and to access the femtocell and a subset of services provided via the femtocell;
updating the access control list to include information related to the at least one subscriber station; and
granting access of the femtocell and the subset of services to the at least one subscriber station based on information in the access control list and at least one predefined access criterion.

36. An apparatus comprising:
a scanner component that scans a frequency spectrum associated with wireless communications to facilitate detection of a wireless communication device in a cell coverage area of a femtocell;
a detector component that detects the wireless communication device in response to the wireless communication device being located within the cell coverage area;
a query component that automatically queries the wireless communication device detected in the cell coverage area to prompt the wireless communication device to request access to the femtocell and a subset of services provided via the femtocell and to be entered on a white list associated with the femtocell;
an update component that updates the access control list to include information related to the wireless communication device; and
a control component that grants access of the femtocell and the subset of services to the wireless communication device based on information in the white list and at least one predefined access criterion.

* * * * *